(12) United States Patent
Ladtkow et al.

(10) Patent No.: US 10,179,023 B2
(45) Date of Patent: Jan. 15, 2019

(54) SHAPED ELECTRODE BIPOLAR RESECTION APPARATUS, SYSTEM AND METHODS OF USE

(71) Applicant: COVIDIEN LP, Mansfield, MA (US)

(72) Inventors: Casey M. Ladtkow, Erie, CO (US); Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/158,255

(22) Filed: May 18, 2016

(65) Prior Publication Data

US 2016/0262828 A1 Sep. 15, 2016

Related U.S. Application Data

(63) Continuation of application No. 13/118,822, filed on Jun. 23, 2011, now Pat. No. 9,358,065.

(51) Int. Cl.
*A61B 18/14* (2006.01)
*A61B 18/00* (2006.01)
*A61B 17/32* (2006.01)

(52) U.S. Cl.
CPC .. *A61B 18/1482* (2013.01); *A61B 17/320016* (2013.01); *A61B 2018/00178* (2013.01);
(Continued)

(58) Field of Classification Search
CPC ........ A61B 18/149; A61B 2018/00601; A61B 2018/00607; A61B 2018/1412; A61B 2018/1475; A61B 2018/1467; A61B 2018/126; A61B 2018/00958; A61B 2018/00178; A61B 2018/00184; A61B 18/1482; A61B 17/320016
See application file for complete search history.

(56) References Cited

U.S. PATENT DOCUMENTS

| | | | |
|---|---|---|---|
| 4,534,347 | A | 8/1985 | Taylor |
| 4,545,375 | A | 10/1985 | Cline |

(Continued)

FOREIGN PATENT DOCUMENTS

| | | |
|---|---|---|
| DE | 9215053 U1 | 4/1993 |
| JP | H11-70123 A | 3/1999 |

(Continued)

OTHER PUBLICATIONS

Japanese Office Action and English language translation from Application No. JP 2012-122674 dated Sep. 6, 2016.
(Continued)

*Primary Examiner* — Eunhwa Kim

(57) ABSTRACT

An electrosurgical instrument is provided and includes a housing configured to connect to a source of bipolar electrosurgical energy and an electrode body coupled to the elongated housing. The electrode body includes an electrode face, first and second bipolar electrodes and a blade. The electrode face is formed on the distal end of the electrode body and includes a longitudinal axis and a transverse axis therethrough. The first and second electrodes have a leading edge and a trailing edge, are formed on opposite sides of the longitudinal axis and connect to opposed electrical potentials. The blade is positioned between the electrodes with at least a portion of the blade extending beyond the electrode face.

20 Claims, 17 Drawing Sheets

(52) U.S. Cl.
CPC .............. *A61B 2018/00184* (2013.01); *A61B 2018/00607* (2013.01); *A61B 2018/00958* (2013.01); *A61B 2018/1412* (2013.01)

(56) References Cited

U.S. PATENT DOCUMENTS

| | | | |
|---|---|---|---|
| 5,300,068 A | 4/1994 | Rosar et al. | |
| 5,401,272 A | 3/1995 | Perkins | |
| 5,441,499 A * | 8/1995 | Fritzsch | A61B 17/00234 |
| | | | 606/45 |
| 5,531,744 A | 7/1996 | Nardella et al. | |
| 5,599,350 A | 2/1997 | Schulze et al. | |
| 5,611,798 A | 3/1997 | Eggers | |
| 5,782,748 A | 7/1998 | Palmer et al. | |
| 5,797,938 A * | 8/1998 | Paraschac | A61B 18/1447 |
| | | | 606/167 |
| 5,810,811 A | 9/1998 | Yates et al. | |
| 5,833,690 A | 11/1998 | Yates et al. | |
| 5,893,863 A | 4/1999 | Yoon | |
| 5,895,386 A * | 4/1999 | Odell | A61B 18/148 |
| | | | 606/42 |
| 6,159,200 A | 12/2000 | Verdura et al. | |
| 6,165,184 A | 12/2000 | Verdura et al. | |
| 6,440,138 B1 * | 8/2002 | Reiley | A61B 50/30 |
| | | | 606/45 |
| 6,645,198 B1 | 11/2003 | Bommannan et al. | |
| 6,692,445 B2 | 2/2004 | Roberts et al. | |
| 6,770,072 B1 | 8/2004 | Truckai et al. | |
| 6,786,906 B1 * | 9/2004 | Cobb | A61B 18/14 |
| | | | 606/37 |
| 6,808,525 B2 * | 10/2004 | Latterell | A61B 18/1442 |
| | | | 606/42 |
| 7,135,018 B2 | 11/2006 | Ryan et al. | |
| 7,241,293 B2 | 7/2007 | Davison | |
| 7,331,957 B2 | 2/2008 | Woloszko et al. | |
| 7,419,488 B2 | 9/2008 | Ciarrocca et al. | |
| 7,422,586 B2 | 9/2008 | Morris et al. | |
| 9,358,065 B2 | 6/2016 | Ladtkow et al. | |
| 2002/0111624 A1 | 8/2002 | Witt et al. | |
| 2002/0120261 A1 | 8/2002 | Morris et al. | |
| 2004/0193146 A1 | 9/2004 | Lee et al. | |
| 2005/0059966 A1 | 3/2005 | McClurken et al. | |
| 2005/0065510 A1 | 3/2005 | Carmel et al. | |
| 2005/0131396 A1 | 6/2005 | Stanczak et al. | |
| 2005/0137662 A1 | 6/2005 | Morris et al. | |
| 2006/0084973 A1 | 4/2006 | Hushka | |
| 2006/0279534 A1 | 12/2006 | Powers et al. | |
| 2007/0016182 A1 | 1/2007 | Lipson et al. | |
| 2007/0078454 A1 | 4/2007 | McPherson | |
| 2007/0244477 A1 | 10/2007 | Santilli et al. | |
| 2007/0260240 A1 | 11/2007 | Rusin | |
| 2008/0294222 A1 | 11/2008 | Schechter | |
| 2009/0125026 A1 | 5/2009 | Rioux et al. | |
| 2009/0157074 A1 | 6/2009 | Livneh | |
| 2009/0206131 A1 | 8/2009 | Weisenburgh, II et al. | |
| 2009/0306658 A1 * | 12/2009 | Nobis | A61B 17/320016 |
| | | | 606/46 |

FOREIGN PATENT DOCUMENTS

| | | |
|---|---|---|
| JP | 2004-528869 A | 9/2004 |
| JP | 2006102513 A | 4/2006 |
| JP | 2007-98135 A | 4/2007 |
| WO | 0226143 A1 | 4/2002 |
| WO | 2008005433 A1 | 1/2008 |
| WO | 2008044000 A1 | 4/2008 |

OTHER PUBLICATIONS

European Search Report dated Dec. 10, 2013 in European Application No. EP 11 17 0965.
Australian Examination Report dated Apr. 30, 2013 in copending Australian Application No. 2012203247.
European Search Report for European Application No. 12004140.5 dated Oct. 5, 2012.
Japanese Office Action and English language translation from Application No. JP 2012-122674 dated Mar. 15, 2016.
Japanese Office Action issued in Appl. No. 2017-049725 dated Mar. 6, 2018, together with English language translation (9 pages).
Final Rejection issued in Japanese Patent Appl. No. 2017-049725, dated Jul. 17, 2018, together with English language translation (7 pages).

* cited by examiner

SHAPED ELECTRODE BIPOLAR RESECTION APPARATUS, SYSTEM AND METHODS OF USE

CROSS-REFERENCE TO RELATED APPLICATIONS

This application is a continuation application of U.S. application Ser. No. 13/118,822, filed on Jun. 23, 2011, the entire contents of which are incorporated herein by reference.

BACKGROUND

1. Technical Field

The present disclosure relates generally to electrosurgical instruments and, more particularly, to an electrosurgical instrument with an electrode body configured for bipolar resection.

2. Background of Related Art

Electrosurgical instruments have become widely used by surgeons in recent years. Accordingly, a need has developed for equipment and instruments which are easy to handle, are reliable and are safe in an operating environment. By and large, most electrosurgical instruments are hand-held instruments, e.g., an electrosurgical pencil, which transfer radio-frequency (RF) electrical or electrosurgical energy to a tissue site. The electrosurgical energy is returned to the electrosurgical source via a return electrode pad positioned under a patient (i.e., a monopolar system configuration) or a smaller return electrode positionable in bodily contact with or immediately adjacent to the surgical site (i.e., a bipolar system configuration). The waveforms produced by the RF source yield a predetermined electrosurgical effect known generally as electrosurgical cutting and fulguration.

In particular, electrosurgical fulguration includes the application of an electric spark to biological tissue, for example, human flesh or the tissue of internal organs, without significant cutting. The spark is produced by bursts of radio-frequency electrical or electrosurgical energy generated from an appropriate electrosurgical generator. Coagulation is defined as a process of desiccating tissue wherein the tissue cells are ruptured and dehydrated/dried. Electrosurgical cutting/dissecting, on the other hand, includes applying an electrical spark to tissue in order to produce a cutting, dissecting and/or dividing effect. Blending includes the function of cutting/dissecting combined with the production of a hemostasis effect. Meanwhile, sealing/hemostasis is defined as the process of liquefying the collagen in the tissue so that it forms into a fused mass.

As used herein the term "electrosurgical pencil" is intended to include instruments that have a handpiece which is attached to an active electrode and that is used to cauterize, coagulate and/or cut tissue. Typically, the electrosurgical pencil may be operated by a handswitch or a foot switch.

As mentioned above, the handpiece of the electrosurgical pencil is connected to a suitable electrosurgical energy source (e.g., generator) that produces the radio-frequency electrical energy necessary for the operation of the electrosurgical pencil. In general, when an operation is performed on a patient with an electrosurgical pencil in a monopolar mode, electrical energy from the electrosurgical generator is conducted through the active electrode to the tissue at the site of the operation and then through the patient to a return electrode. The return electrode is typically placed at a convenient place on the patient's body and is attached to the generator by a conductive material. Typically, the surgeon activates the controls on the electrosurgical pencil to select the modes/waveforms to achieve a desired surgical effect. Typically, the "modes" relate to the various electrical waveforms, e.g., a cutting waveform has a tendency to cut tissue, a coagulating wave form has a tendency to coagulate tissue, and a blend wave form tends to be somewhere between a cut and coagulate wave from. The power or energy parameters are typically controlled from outside the sterile field which requires an intermediary like a circulating nurse to make such adjustment.

When an operation is performed on a patient with an electrosurgical pencil in a bipolar mode, the electrode face includes at least one pair of bipolar electrodes and electrical energy from the electrosurgical generator is conducted through tissue between the pair of bipolar electrodes.

A typical electrosurgical generator has numerous controls for selecting an electrosurgical output. For example, the surgeon can select various surgical "modes" to treat tissue: cut, blend (blend levels 1-3), low cut, desiccate, fulgurate, spray, etc. The surgeon also has the option of selecting a range of power settings typically ranging from 1-300 W. As can be appreciated, this gives the surgeon a great deal of variety when treating tissue. Surgeons typically follow preset control parameters and stay within known modes and power settings and electrosurgical pencils include simple and ergonomically friendly controls that are easily selected to regulate the various modes and power settings Existing electrosurgical instrument systems allow the surgeon to change between two pre-configured settings (i.e., coagulation and cutting) via two discrete switches disposed on the electrosurgical pencil. Other electrosurgical instrument systems allow the surgeon to increment the power applied when the coagulating or cutting switch of the instrument is depressed by adjusting or closing a switch on the electrosurgical generator. The surgeon then needs to visually verify the change in the power being applied by looking at various displays and/or meters on the electrosurgical generator. In other words, all of the adjustments to the electrosurgical instrument and parameters being monitored during the use of the electrosurgical instrument are typically located on the electrosurgical generator. As such, the surgeon must continually visually monitor the electrosurgical generator during the surgical procedure.

Electrosurgical instrument systems have been increasingly provided with coupling and/or connecting systems (e.g., a plug) for removably connecting the electrosurgical instrument to the electrosurgical generator. Typically, the electrosurgical instrument is provided with a so called "male" connector while the electrosurgical generator is provided with the corresponding "female" connector. Connectors may include an identification device to provide specific identification information about the device connected thereto. Other systems include device detection algorithms that interface with the identification device or that determine the type of device by measuring a specific characteristic of the electrosurgical instrument.

Since electrosurgery requires controlled application of radio frequency energy to an operative tissue site, it is important that the appropriate electrosurgical generator be correctly and/or properly mated with the electrosurgical instrument for the specific electrosurgical procedure. Electrosurgical instruments are typically configured such that power output can be adjusted without the surgeon having to turn his or her vision away from the operating site and toward the electrosurgical generator.

SUMMARY

The present disclosure relates to an electrosurgical instrument configured for performing a bipolar resection procedure. The electrosurgical instrument includes a housing configured to connect to a source of bipolar electrosurgical energy and an electrode body coupled to the elongated housing. The electrode body includes an electrode face, first and second bipolar electrodes and a blade. The electrode face is formed on the distal end of the electrode body and includes a longitudinal axis and a transverse axis therethrough. The first and second electrodes have a leading edge and a trailing edge, are formed on opposite sides of the longitudinal axis and connect to opposed electrical potentials. The blade is positioned between the electrodes with at least a portion of the blade extending beyond the electrode face.

The blade may be positioned along the longitudinal axis and the transverse axis such that the first and second bipolar electrodes treat tissue before and after the blade transects tissue.

The first and second electrodes may be symmetrical along the longitudinal axis and/or the transverse axis, or the first and second electrodes may be asymmetrical. In one embodiment asymmetrical first and second bipolar electrodes define a wide portion and a small portion, wherein the wide portion is proximate the leading edges of the first and second bipolar electrodes. In yet another embodiment, the first and second bipolar electrode may be symmetrical to each other about the longitudinal centerline.

The blade may be symmetrical along the longitudinal axis and/or the transverse axis and may further includes leading and trailing cutting edges. The blade may also be deployable between an undeployed position and a plurality of deployed position wherein at least one of the deployed positions is a cut position. The electrode body may include an actuator operably connected between the blade and the electrode body and the actuator may actuate the blade between an undeployed position and the plurality of deployed positions.

In yet another embodiment, the electrosurgical pencil further includes at least one actuator that actuates the electrode body in at least one of a Yaw, Pitch and Rotate direction relative to a longitudinal axis defined through a shaft that couples the electrode body to the housing.

The present disclosure also recites an electrosurgical instrument including a housing configured to connect to a source of electrosurgical energy, an electrode body coupled to the housing and at least one activation switch supported on the housing. The electrode body includes an electrode face formed on a distal end of the electrode body, first and second electrodes formed on the electrode face and a blade positioned about midway between the first electrode and the second electrode. A portion of the blade is configured to extend distally beyond the electrode face. The activation switch, upon activation thereof, selectively completes a control loop extending from the source of electrosurgical energy and provides opposing electrical potentials between the first and second electrodes.

The present disclosure also relates to an electrosurgical system including a source of electrosurgical energy and an electrosurgical instrument. The electrosurgical instrument includes a housing configured to connect to a source of electrosurgical energy, an electrode body coupled to the housing with an electrode face formed on a distal end of the electrode body and at least one activation switch supported on the housing. The electrode face includes a longitudinal axis and a transverse axis defined therethrough, first and second electrodes formed on opposite sides of the longitudinal axis and configured to connect to opposed electrical potentials and a blade positioned between the first and second electrodes. At least a portion of the blade may extend beyond the electrode face. The activation switch is configured to selectively complete a control loop that provides opposing electrical potentials, generated by the source of electrosurgical energy, between the first and second electrodes.

The blade is positioned along the longitudinal axis and transverse axis such that the first and second electrodes are operable to treat tissue before and after the blade transects tissue. The first and second bipolar electrodes may be symmetrical along the longitudinal axis and/or the first electrode and the second electrode may be symmetrical about the transverse axis Alternatively, the first electrode and the second electrode may be asymmetrical and may define a wide portion and a small portion, wherein the wide portion is proximate the leading edges of the first and second electrodes.

The blade may be symmetrical along the longitudinal axis and the transverse axis with leading and trailing cutting edges. The blade may be deployable between an undeployed position and a plurality of deployed positions with at least one of the deployed positions being a cut position.

The electrode body may include an actuator operably connected between the blade and the electrode body and configured to actuate the blade between the undeployed position and the deployed positions.

The electrosurgical instrument may further include one or more actuators that actuate the electrode body in at least one of a Yaw, Pitch and/or rotate direction relative to a longitudinal axis defined by a shaft that couples the electrode body to the housing.

The present disclosure also recites methods for performing an electro-mechanical resection procedure comprising the steps of: selecting a resection line along patient tissue; providing a source of electrosurgical energy; providing an electrosurgical instrument including: a housing configured to connect to the source of electrosurgical energy and an electrode body coupled to the housing. The electrode body includes an electrode face formed on a distal end of the electrode body having a longitudinal axis and a transverse axis defined therethrough and first and second electrodes formed on opposite sides of the longitudinal axis and configured to connect to opposed electrical potentials. Each of the first and second electrodes including a leading edge and a trailing edge and a blade positioned between the first electrode and the second electrodes. At least a portion of the blade is configured to extend beyond the electrode face. The method also includes the steps of connecting the source of electrosurgical energy to the first and second electrodes thereby generating opposing electrical potentials between the first and second electrodes; and drawing the electrosurgical instrument along the longitudinal axis and across the resection line in a first direction and simultaneously cutting tissue with the blade in the first direction, treating uncut tissue along the resection and treating cut tissue along the resection line.

The method may further include the steps of repositioning the blade such that the blade does not extend beyond the electrode face and focusing current flow along the walls of the cut tissue of the along the resection line with the electrosurgical instrument to coagulate tissue.

In another embodiment, the blade may include leading and trailing cutting edges and the method may further include the step of drawing the electrosurgical instrument along the longitudinal axis and across the resection line in a second direction opposite the first direction and simultaneously cutting tissue with the blade in the second direction thereby treating uncut tissue along the resection and treating cut tissue along the resection line.

In a further embodiment, the method may include the steps of selecting a first blade position, wherein at least a portion of the blade extends beyond the electrode face in the first blade position and positioning the blade in the first blade position.

BRIEF DESCRIPTION OF THE DRAWINGS

The accompanying drawings, which are incorporated in and constitute a part of this specification, illustrate embodiments of the invention, and together with a general description of the invention given above, and the detailed description of the embodiments given below, serve to explain the principles of the invention.

DETAILED DESCRIPTION

Figure 1:
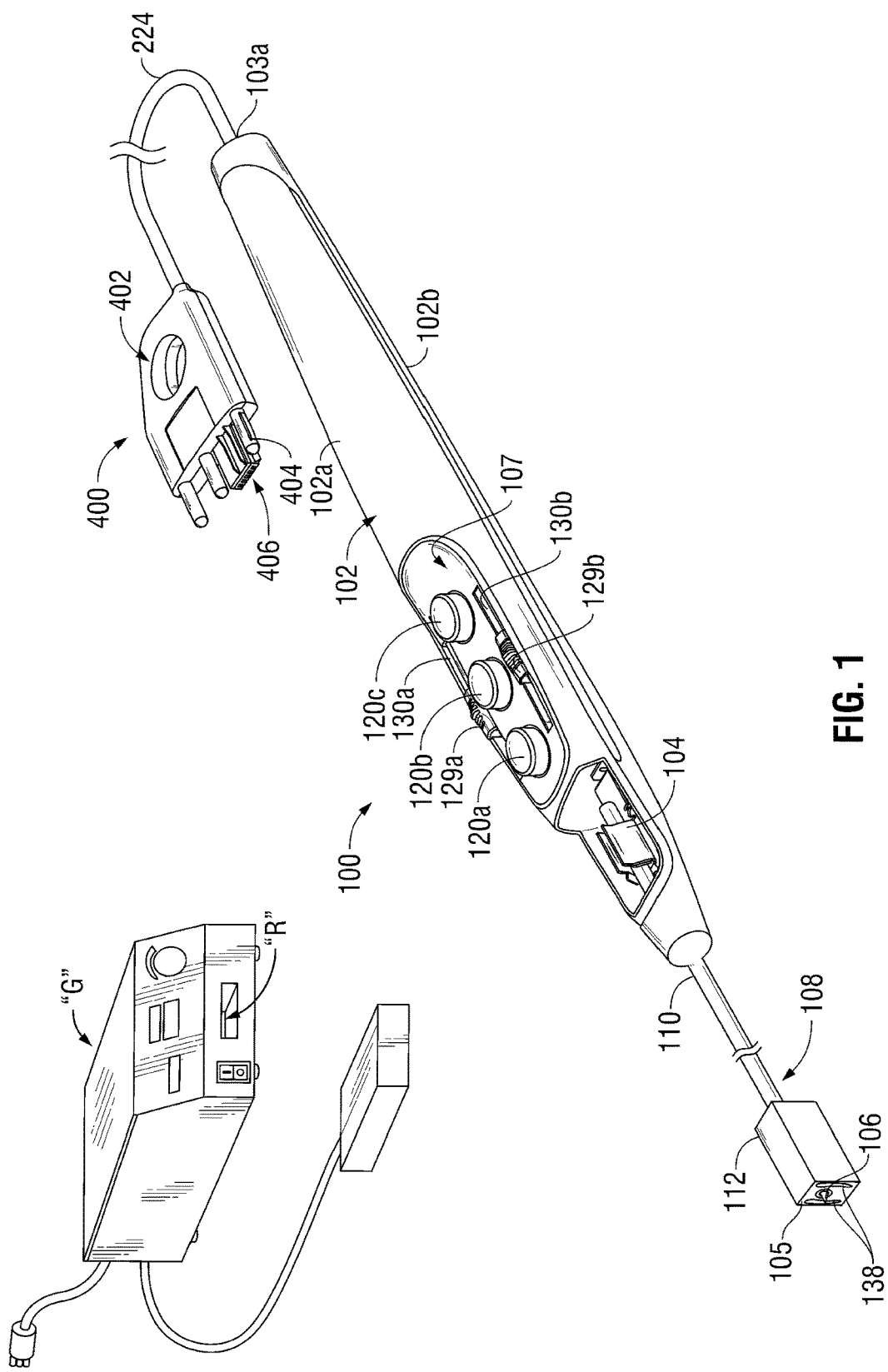
FIG. 1 is a perspective view of an electrosurgical system including an electrosurgical pencil configured for bipolar resection in accordance with an embodiment of the present disclosure.

Particular embodiments of the presently disclosed electrosurgical pencil configured for bipolar resection are described in detail with reference to the drawing figures wherein like reference numerals identify similar or identical elements. As used herein, the term "distal" refers to that portion which is further from the user while the term "proximal" refers to that portion which is closer to the user or clinician. The term "leading edge" refers to the most forward edge with respect to the direction of travel while the term "trailing edge" refers to the edge opposite the leading edge with respect to the direction of travel.

FIG. 1 sets forth a perspective view of an electrosurgical system including an electrosurgical pencil 100 constructed for bipolar resection in accordance with one embodiment of the present disclosure. While the following description is directed towards electrosurgical pencils for bipolar resection, the features and concepts (or portions thereof) of the present disclosure may be applied to any electrosurgical type instrument, e.g., forceps, suction coagulators, vessel sealers, wands, etc. The construction, functionality and operation of electrosurgical pencils, with respect to use for bipolar resection, is described herein. Further details of the electrosurgical pencil are provided in commonly-owned U.S. Pat. No. 7,156,842 to Sartor et al.

Figure 2:
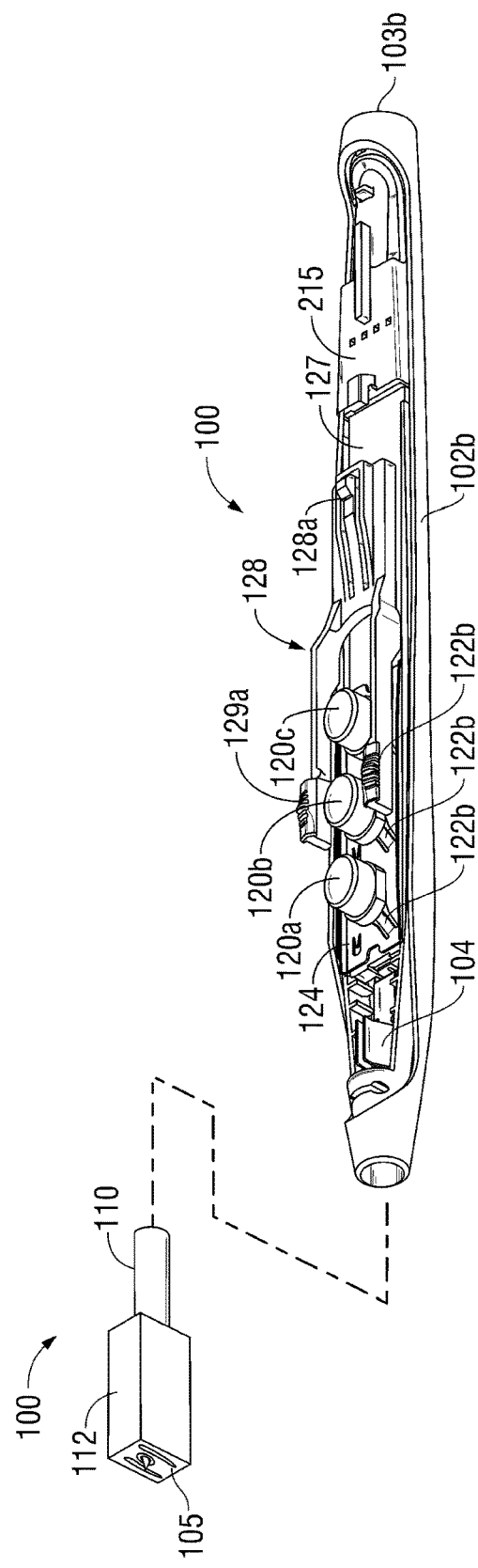
FIG. 2 is a front, top perspective view of the electrosurgical pencil of FIG. 1, with a top-half shell of the housing removed.

As seen in FIGS. 1 and 2, electrosurgical pencil 100 includes an elongated housing 102 having a top-half shell portion 102a and a bottom-half shell portion 102b. The elongated housing 102 includes a distal opening 103b, through which a shaft 110 extends, and a proximal opening 103a, through which connecting wire 224 (see FIG. 1) extends. Top-half shell portion 102a and bottom-half shell portion 102b may be bonded together using any suitable method, e.g., sonic energy, adhesives, snap-fit assemblies, etc.

Electrosurgical pencil 100 further includes an end effector receptacle 104 disposed at a distal end of housing 102, and a replaceable end effector 108 operatively and removably connectable to end effector receptacle 104. Replaceable end effector 108 may be in the form of a needle, loop, blade and/or wand. In the present application replaceable end effector 108 includes an electrode body 112 at a distal end thereof with at least one pair of bipolar electrodes and a blade 106 extending distally from the electrode body 112. Electrode body 112, positioned on the distal end of the shaft 110, is electrically connected to generator "G" through electrical conductors formed in the shaft 110, elongated housing 102, connecting wire 224 and plug assembly 400. Generator "G" may be incorporated into the elongated housing 102 and powered by an internal energy supply, e.g., battery or other energy storage device, fuel cell or other energy generation device or any other suitable portable power source.

Shaft 110 is selectively retained by end effector receptacle 104 disposed in housing 102. Shaft 110 may include a plurality of conductive traces or wires along the length of the shaft 100. The conductive traces or wires may be fabricated from a conductive type material, such as, for example, stainless steel, or shaft may be coated with an electrically conductive material. End effector receptacle 104 is fabricated from electrically conductive materials or includes electrically conductive contacts configured to couple with the plurality of conductive traces or wires of the shaft 110. End effector receptacle 104 is electrically connected to voltage divider network 127 (FIGS. 2 and 4) as explained in more detail below. Conductive traces or wires of the shaft electrically connect to the electrode body 112.

Bipolar electrodes 138 are configured to deliver electrosurgical energy along a resection line to treat tissue positioned before the blade 106 (e.g., uncut tissue before resection), to treat tissue during and at the point of resection (e.g., while tissue is cut) and to treat tissue after resection (e.g., cut tissue along the resection line after resection).

As seen in FIG. 1, electrosurgical pencil 100 may be coupled to a conventional electrosurgical generator "G" via a plug assembly 400 (see FIG. 3), as will be described in greater detail below.

For the purposes herein, the terms "switch" or "switches" includes electrical actuators, mechanical actuators, electromechanical actuators (rotatable actuators, pivotable actuators, toggle-like actuators, buttons, etc.) or optical actuators.

Electrosurgical pencil 100 includes at least one activation switch, and may include three activation switches 120a-120c, each of which extends through top-half shell portion 102a of elongated housing 102. Each activation switch 120a-120c is operatively supported on a respective tactile element 122a-122c provided on a switch plate 124, as illustrated in FIG. 2. Each activation switch 120a-120c controls the transmission of RF electrical energy supplied from generator "G" to bipolar electrodes 138 on electrode face 105 of electrode body 112. More particularly, switch plate 124 is positioned on top of a voltage divider network 127 (hereinafter "VDN 127") such that tactile elements 122a-122c are operatively associated therewith. VDN 127 (e.g., here shown in FIG. 2 as a film-type potentiometer) forms a switch closure. For the purposes herein, the term "voltage divider network" relates to any known form of resistive, capacitive or inductive switch closure (or the like) which determines the output voltage across a voltage source (e.g., one of two impedances) connected in series. A "voltage divider" as used herein relates to a number of resistors connected in series which are provided with taps at certain points to make available a fixed or variable fraction of the applied voltage. Further details of electrosurgical pencil control are provided in above-mentioned U.S. Pat. No. 7,503,917 to Sartor et al.

Figure 3:
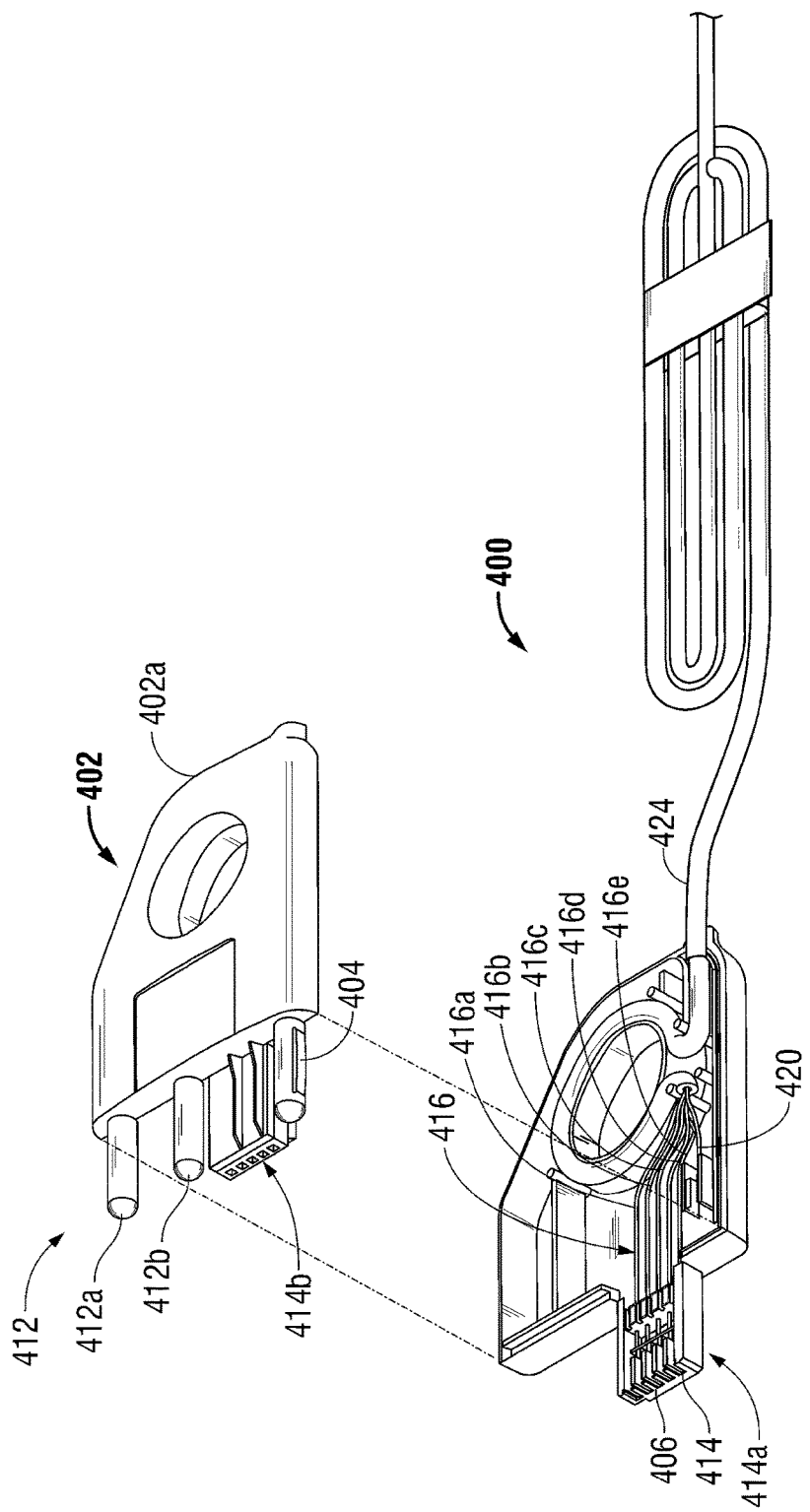
FIG. 3 is a perspective view of the plug assembly of FIG. 1, with a top-half shell section removed therefrom.

In use, depending on which activation switch 120a-120c is depressed a respective tactile element 122a-122c is pressed into contact with VDN 127 and a characteristic signal is transmitted to electrosurgical generator "G" via control wires 416 (see FIG. 3). In one embodiment, three control wires 416a-416c (one for each activation switch 120a-120c, respectively) are provided. Control wires 416a-416c are electrically connected to switches 120a-120c via a control terminal 215 (see FIG. 2) which is operatively connected to VDN 127. By way of example only, electrosurgical generator "G" may be used in conjunction with the device wherein generator "G" includes a circuit for interpreting and responding to the VDN 127 settings.

Activation switches 120a, 120b, 120c are configured and adapted to control the mode and/or "waveform duty cycle" to achieve a desired surgical intent. For example, a first activation switch 120a can be set to deliver a characteristic signal to electrosurgical generator "G" which, in turn, transmits a duty cycle and/or waveform shape that produces a first desirable resection effect. Meanwhile, second activation switch 120b can be set to deliver a characteristic signal to electrosurgical generator "G" which, in turn, transmits a duty cycle and/or waveform shape that produces a second desirable resection effect. Finally, third activation switch 120c can be set to deliver a characteristic signal to electrosurgical generator "G" which, in turn, transmits a duty cycle and/or waveform shape that produces a third electrosurgical effect/function. Desirable resection effects may include a mode for bipolar coagulation and/or cauterization with an undeployed blade, a mode for bipolar resection with a partially deployed blade, a mode for bipolar resection with a fully deployed blade, a mode for monopolar resection and a mode for resection with blended energy delivery (monopolar and bipolar modes), as will be described in greater detail hereinbelow.

As seen in FIG. 3, fourth and fifth wires (e.g., first RF line 416d and second RF line 416e) are provided and electrically connect to bipolar electrodes 138 formed on electrode body 112. Since first RF line 416d and second RF line 416e are directly connected to bipolar electrodes 138 on electrode body 112, first RF line 416d and second RF line 416e bypass the VDN 127 and are isolated from VDN 127 and control wires 416a-416c. By directly connecting the first RF line 416d and second RF line 416e to corresponding bipolar electrodes 138 on the electrode body 112 and isolating the VDN 127 from the RF energy transmission, the electrosurgical current does not flow through VDN 127. This in turn, increases the longevity and life of VDN 127 and/or activation switches 120a, 120b, 120c.

Figure 4:
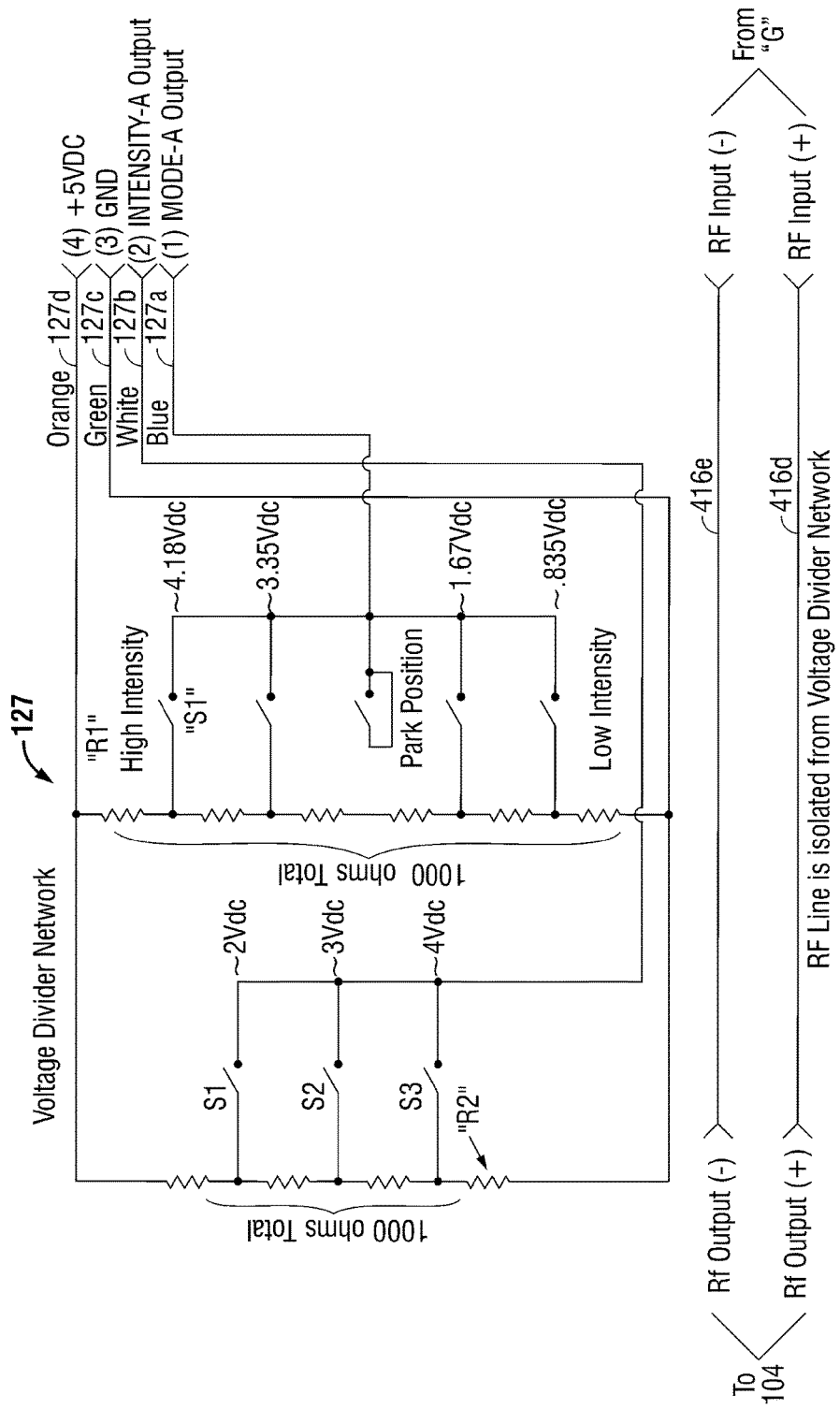
FIG. 4 is a schematic illustration of the voltage divider network of the present disclosure.

With reference to FIG. 4, VDN 127 is shown and includes a first transmission line 127a configured to operate the various modes of electrosurgical pencil 100; a second transmission line 127b configured to operate the various intensities of electrosurgical pencil 100; a third transmission line 127c configured to function as a ground for VDN 127; and a fourth transmission line 127d which transmits up to about +5 volts to VDN 127.

First RF line 416d and second RF line 416e are isolated from or otherwise completely separate from VDN 127. In particular, first RF line 416d and second RF line 416e extends directly from the RF input or generator "G" to the bipolar electrodes on the electrode body 112.

By way of example only, VDN 127 may include a plurality of resistors "R1" (e.g., six resistors), connected in a first series between third transmission line 127c and fourth transmission line 127d. The first series of resistors "R1" may combine to total about 1000 ohms of resistance. The first series of resistors "R1" are each separated by a first set of switches "S1". Each switch of the first set of switches "S1" may be electrically connected between adjacent resistors "R1" and first transmission line 127a of VDN 127. In operation, depending on which switch or switches of the first set of switches "S1" is/are closed, a different mode of operation for electrosurgical pencil 100 is activated.

Resection may be performed with electrosurgical energy including waveforms having a duty cycle from about 10% to about 100%. The dual effect of coagulating and cauterizing, as described herein, may be performed with a waveform having a duty cycle from about 10% to about 100%. To increase the depth of coagulation may require a waveform with a duty cycle from about 50% to 100%. It is important to note that these percentages are approximated and may be customized to deliver the desired surgical effect for various tissue types and characteristics.

In one embodiment, the waveforms provided to the bipolar electrosurgical pencil 100 may be dynamically controlled by the generator "G". For example, the mode of operation provided by switches S1, S2, S3 may indicate a range of operation for the generator "G". Generator "G" provides a waveform within the specified range of operation wherein the waveform is dynamically changed based on a parameter, wherein the parameter may be related to one of energy delivery, the target tissue and the duration of energy delivery. The parameter may be obtained from a source external to the generator "G", such as, a measured parameter or clinician provided parameter, or the parameter may include an internal parameter obtained, measured or determined by the generator "G".

As seen throughout FIG. 2, electrosurgical pencil 100 further includes an intensity controller 128 slidingly supported on or in elongated housing 102. Intensity controller 128 may be configured to function as a slide potentiometer, sliding over and along VDN 127 wherein the distal-most position corresponds to a relative high intensity setting, the proximal-most position corresponds to a low intensity settings with a plurality of intermediate positions therebetween. As can be appreciated, the intensity settings from the proximal end to the distal end may be reversed, e.g., high to low.

The intensity settings are typically preset and selected from a look-up table based on a choice of electrosurgical instruments/attachments, desired surgical effect, surgical specialty and/or surgeon preference, the type of electrode body 112 and the arrangement of the bipolar electrodes on the electrode face 105. The selection of the electrode body 112, the intensity setting and duty cycle determines the surgical effect. The settings may be selected manually by the user or automatically. For example, the electrosurgical generator "G" may automatically determine the type of electrode body 112 on the distal end of replaceable end effector 108 and a predetermined intensity value may be selected and subsequently adjusted by the user or the electrosurgical generator "G".

Turning now to FIG. 3, a detailed discussion of plug assembly 400 is provided. Plug assembly 400 includes a housing portion 402 and a connecting wire 424 that electrically interconnects the housing portion 402 and the control terminal 215 in the electrosurgical pencil 100 (see FIG. 2). Housing portion 402 includes a first half-section 402a and a second half-section 402b operatively engageable with one another, e.g., via a snap-fit engagement. First half-section 402a and second half-section 402b are configured and adapted to retain a common power pin 404 and a plurality of electrical contacts 406 therebetween.

Common power pin 404 of plug assembly 400 extends distally from housing portion 402 at a location between first half-section 402a and second half-section 402b. Common power pin 404 may be positioned to be off center, i.e., closer to one side edge of housing portion 402 than the other. Plug assembly 400 further includes at least one a pair of position pins 412 also extending from housing portion 402. Position pins 412 may be positioned between the first half-section 402a and the second half-section 402b of housing portion 402 and are oriented in the same direction as common power pin 404. A first position pin 412a is positioned in close proximity to a center of housing portion 402 and a second position pin 412b is positioned to be off center and in close proximity to an opposite side edge of housing portion 402 as compared to common power pin 404. First position pin 412a, second position pin 412b and common power pin 404 may be located on housing portion 402 at locations which correspond to pin receiving positions (not shown) of a connector receptacle "R" of electrosurgical generator "G" (see FIG. 1).

Plug assembly 400 further includes a prong 414 extending from housing portion 402. In particular, prong 414 includes a body portion 414a extending from second half-section 402b of housing portion 402 and a cover portion 414b extending from first half-section 402a of housing portion 402. In this manner, when the first half-section 402a and the second half-section 402b are joined to one another, cover portion 414b of prong 414 encloses the body portion 414a. Prong 414 may be positioned between common power pin 404 and first position pin 412a. Prong 414 is configured and adapted to retain electrical contacts 406 therein such that a portion of each electrical contact 406 is exposed along a front or distal edge thereof. While five electrical contacts 406 are shown, any number of electrical contacts 406 can be provided, including and not limited to two, six and eight. Prong 414 may be located on housing portion 402 at a location that corresponds to a prong receiving position (not shown) of connector receptacle "R" of electrosurgical generator "G" (see FIG. 1).

Since prong 414 extends from second half-section 402b of housing portion 402, housing portion 402 of plug assembly 400 will not enter connector receptacle "R" of electrosurgical generator "G" unless housing portion 402 is in a proper orientation. In other words, prong 414 functions as a polarization member. This ensures that common power pin 404 is properly received in connector receptacle "R" of electrosurgical generator "G".

Connecting wire 424 includes a power supplying wire 420 electrically connected to common power pin 404, control wires 416a-416c electrically connected to a respective electrical contact 406, and first RF line 416d and second RF line 416e electrically connected to a respective electrical contact 406.

Figure 5:
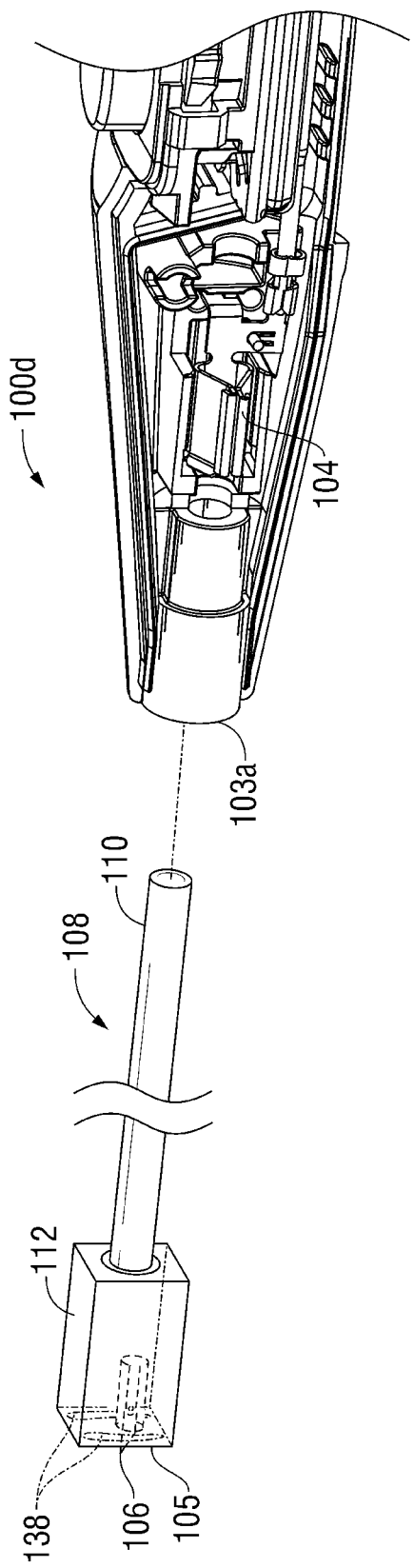
FIG. 5 is a partial, cross-sectional view of a distal end of an electrosurgical pencil, in accordance an embodiment of the present disclosure.

Turning now to FIG. 5, distal portion of electrosurgical pencil 100 is shown generally as 100d. Shaft 110 is configured to engage end effector receptacle 104. Shaft 110 and end effector receptacle 104 are configured to provide a plurality of suitable electrical connections therebetween to facility the delivery of electrosurgical energy from the electrosurgical generator "G" (See FIG. 1) to the electrode body 112.

At least a portion of the shaft 110 is inserted into distal opening 103a of the elongated housing 102 to engage end effector receptacle 104. End effector receptacle 104 is configured to mechanically and electrically couple the shaft 110 to the elongated housing 102. Electrical connections may include one or more electrical connectors (or electrical connector pairs) that connect to the electrode body 112 for power, control and/or sensing. For example, end effector receptacle 104 may provide one or more electrical connector pairs that provide bipolar electrosurgical energy, electrical power and control connections for blade actuation, and/or positioning and position sensing and electrical connectors for one or more sensing devices (e.g., a temperature sensor, a pressure sensor, a position sensor, etc.). Shaft 110 and end effector receptacle 104 may include a locking device, such as, for example, a shaft locking pin that slides into and engages a shaft locking pin receptacle (not explicitly shown). Any suitable securing and/or locking apparatus may be used to releasably secure the shaft 110 to the elongated housing 102.

As described herein, the shaft 110, with the electrode body 112 attached to the distal end thereof, is interchangeable with the elongated housing 102. In other embodiments, shaft 110 is integrated into the elongated housing 102 and is not replaceable. For example, shaft 110 may include at least one mechanical linkage integrated into the elongated housing 102 configured to adjust the depth and/or position of the blade 106 with respect to the electrode face 105. The mechanical linkages may connect between an adjustment mechanism (e.g., a slide, dial or selector) on the housing and an articulation mechanism (deployment actuator and/or position controller) on the distal end of shaft 110 or in the electrode body 112.

Figure 6:
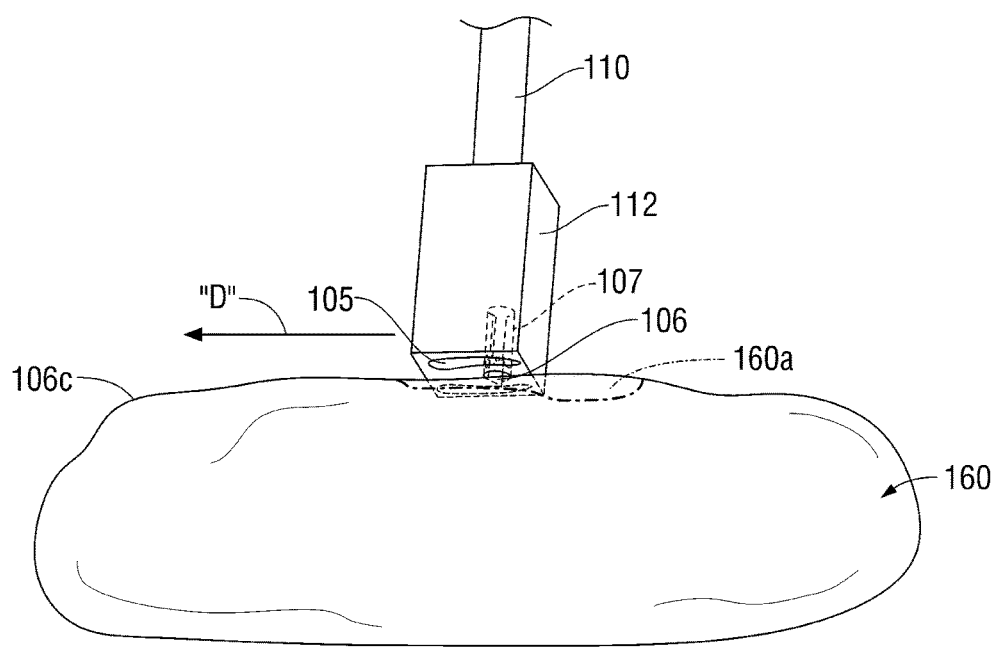
FIG. 6 is a side view of an electrode body of an electrosurgical pencil during a resection procedure according to one embodiment of the present disclosure.

FIG. 6 is a perspective view, in partial cross-section, illustrating an electrode body 112 during a resection procedure. The electrode face 105 on the distal end of the electrode body 112 is positioned in contact with tissue 160 along a resection line 160c. As the electrode body 112 is drawn across the tissue 160 in a direction of travel "D", the bipolar electrodes (See FIGS. 7A-10B) on the electrode face 105 treats tissue 160 along the resection line 160a by delivering bipolar electrosurgical energy and the blade 106 resects at least a portion of the treated tissue 160a. The position of the blade 106, with respect to the electrode body, as discussed hereinbelow, is selected such that the electrode body 112 electrosurgically treats uncut tissue prior to resection and electrosurgically treats cut tissue after resection.

Figure 7A:
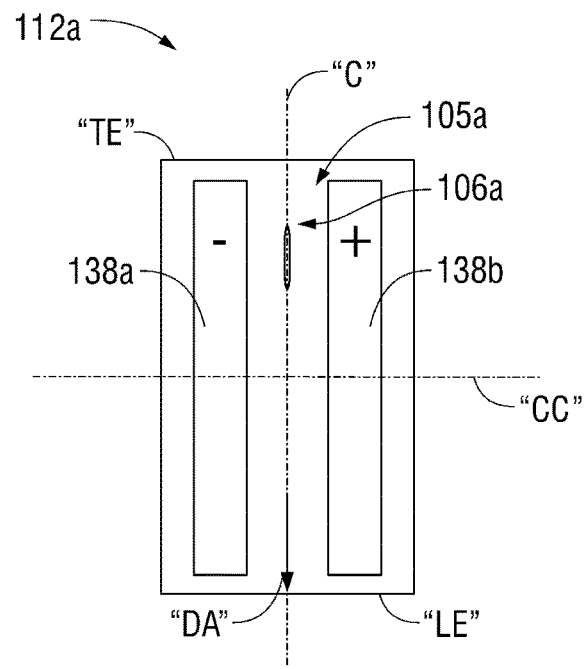
FIG. 7A is a bottom view of the electrode body, including the electrode face, of the electrosurgical pencil of FIG. 1.
Figure 7B:
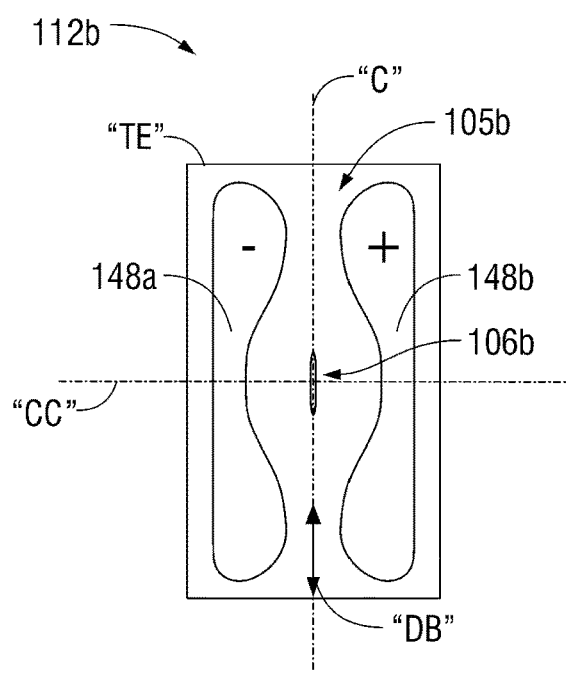
FIG. 7B is a bottom view of an electrode body including a bidirectional electrode face, in accordance with another embodiment of the present disclosure.

FIGS. 7A and 7B are bottom views of different electrode bodies 112a, 112b each illustrating a respective electrode face 105a, 105b with substantially symmetric bipolar electrode arrangements. FIG. 7A illustrates a first bipolar electrode 138a and a second bipolar electrode 138b each substantially rectangular and positioned parallel and adjacent a respective edge of the electrode face 105a. The first bipolar electrode 138a and the second bipolar electrode 138b are substantially symmetric with respect to each other about longitudinal centerline "C" and substantially symmetric with respect to each other about transverse line "CC". Mechanical blade 106a is positioned on or adjacent the longitudinal centerline "C" and between the first bipolar electrode 138a and the second bipolar electrodes 138b. Blade 106a is positioned adjacent the trailing edge "TE", wherein the trailing edge "TE" is opposite the leading edge "LE" and the leading edge "LE" is positioned toward the direction of travel "DA".

In use, as discussed above and illustrated in FIG. 6, electrode face 105a is drawn across tissue 160 in the direction of travel "DA". The leading portion of the first and second bipolar electrodes 138a, 138b (e.g., the portion of the bipolar electrodes 138a, 138b adjacent the leading edge "LE" of the electrode face 105a) contacts untreated and/or undertreated tissue and conducts bipolar electrosurgical currents therethrough. The middle portion of the first and second bipolar electrodes 138a, 138b (i.e., adjacent the transverse line "CC") and the portion of the bipolar electrodes 138a, 138b adjacent the trailing edge "TE" also conduct electrosurgical current therebetween. As the electrode face 105a is drawn across tissue 160 in the direction of travel "DA", tissue adjacent the blade 106a, after having been treated by the leading and middle portions of respective first and second bipolar electrodes 138a, 138b is cut by the blade 106a.

FIG. 7B illustrates an electrode body 112b, according to another embodiment of the present disclosure, with an electrode face 105b including a first bipolar electrode 148a and a second bipolar electrode 148b. Each bipolar electrode 148a, 148b includes an outward longitudinal edge substantially parallel and adjacent respective longitudinal side of the electrode body 112b. The first bipolar electrode 148a and the second bipolar electrode 148b are substantially symmetric with respect to each other about longitudinal centerline "C" and substantially symmetric with respect to the transverse line "CC". The blade 106b, with bi-directional cutting surfaces, is positioned between the first and second bipolar electrodes 148a, 148b and adjacent the intersection of the longitudinal centerline "C" and the cross-directional centerline "CC" (e.g., positioned approximately midway between the leading edge "LE" and the trailing edge "TE"). The first bipolar electrode 148a and the second bipolar electrode 148b each include one or more arcuate edges, directed toward a longitudinal centerline "C", and curving radially inward toward the longitudinal centerline "C" along a substantial portion of the electrode face 105b.

In use, the electrode face 105b may be used bi-directionally along the direction of travel "DB". The symmetry of the electrode face 105b, with respect to the longitudinal centerline "C" and the transverse line "CC", with the blade 106b being substantially centered therebetween, produces substantially similar results in either direction of travel "DB".

Figure 8A:
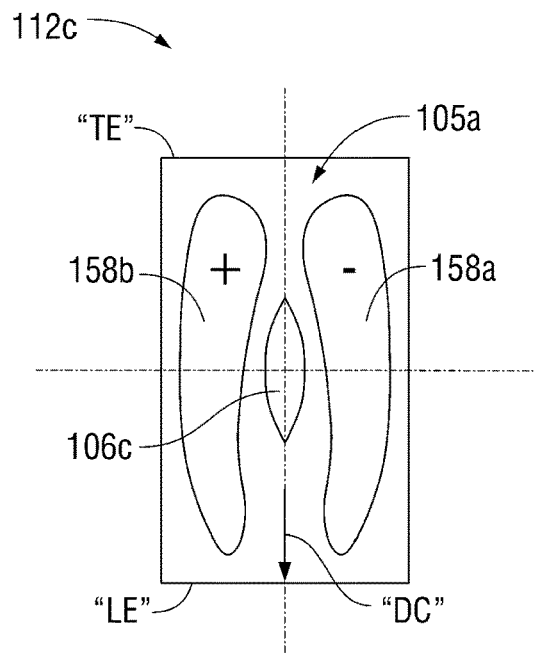
FIG. 8A is a bottom view of an electrode body including a unidirectional electrode face, in accordance with another embodiment of the present disclosure.
Figure 8B:
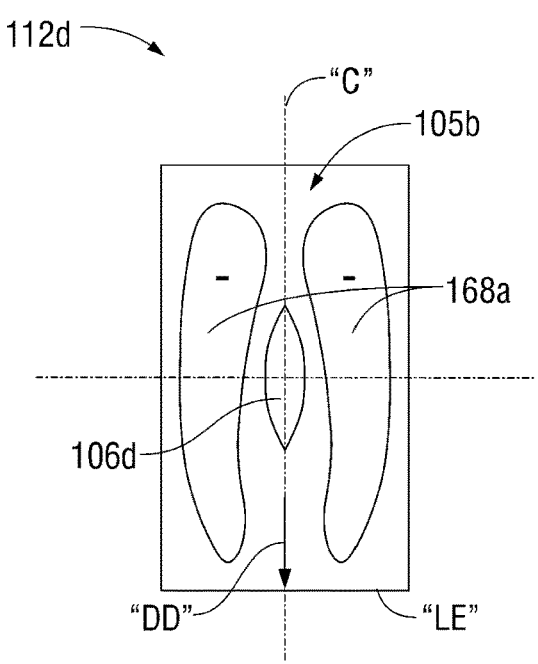
FIG. 8B is a bottom view of an electrode body including a unidirectional electrode face with a conductive blade, in accordance with another embodiment of the present disclosure.

FIGS. 8A and 8B are bottom views of electrode bodies 112c, 112d illustrating electrode faces 105c, 105d, respectively, with unidirectional bipolar arrangements. FIG. 8A illustrates a first bipolar electrode 158a and a second bipolar electrode 158b, each with inner and outer arcuate edges, wherein the spacing therebetween and the cross-directional width thereof are selected to generate a uniformed current density in tissue along the longitudinal length.

At any given point along the longitudinal length of the first and second bipolar electrodes 158a, 158b, the current density in tissue is related to the impedance of the tissue, the contact surface between tissue and the first and second bipolar electrodes 158a, 158b and the spacing therebetween. As the electrode face 105c is drawn across tissue in direction "DC", the bipolar electrosurgical energy generated by electrosurgical currents passing between the first and second bipolar electrodes 158a, 158b treats tissue thereby changing at least one tissue property thereof (e.g., an increase in impedance). A change in a tissue property may change the contact quality between the first and second bipolar electrodes 158a, 158b and the tissue.

The term "contact quality" with respect to the present application refers to the overall quality of the electrical connection between the first and/or second bipolar electrodes 158a, 158b and tissue and the ability of the electrical connection to conduct electrical current therebetween. The factors that determine contact quality may include the amount and percentage of contact between tissue and the first and/or second bipolar electrodes 158a, 158b and the impedance and/or resistance associated with the amount and percentage of contact.

To compensate for any change in a tissue property, the cross-directional width and the spacing between the first and second bipolar electrodes 158a, 158b both vary longitudinally. The width of the portion of the first and second bipolar electrodes 158a, 158b adjacent the leading edge "LE" is a minimum. The cross-directional width of the first and second bipolar electrodes 158a, 158b gradually increase between the portion adjacent the leading edge "LE" and the portion adjacent the blade 106c. The maximum cross-directional width of the first and second bipolar electrodes 158a, 158b is adjacent the trailing edge of the blade 106c (i.e., after the tissue is cut by the blade 106c)

The transverse spacing between the first and second bipolar electrodes 158a, 158b gradually increases from the portion of the first and second bipolar electrodes 158a, 158b adjacent the leading edge "LE" to a maximum distance adjacent the leading edge of the blade 106c. The transverse spacing gradually decreases from the leading edge of the blade 106c to the trailing edge of the blade 106c.

Current pathways, generated through tissue between the first and second bipolar electrodes 158a, 158b, are fundamentally different in uncut tissue (e.g., tissue leading the cutting surface of the blade) and cut tissue (e.g., tissue trailing the cutting surface of the blade). In uncut tissue, the electrosurgical currents that flow between the first and second bipolar electrodes 158a, 158b travel in current pathways along or adjacent surface tissue. As the impedance of the surface tissue and the tissue adjacent the surface increases, the electrosurgical currents, seeking a path of less resistance, penetrate further below the surface tissue. Ideally (but not necessarily), the electrosurgical currents generated in tissue prior to being cut by the blade 106c fully coagulate tissue to a depth that exceeds the depth of the blade 106c.

After the blade 106c cuts tissue, the tissue structure along the resection line changes (due to being cut) and the current pathways used by the electrosurgical currents prior to the cut (along and adjacent the surface of tissue) are severed by the resection line. As such, the electrosurgical currents generated through the cut tissue and between the portion of the first and second bipolar electrodes 158a, 158b positioned between cut tissue (e.g., between the trailing edge "TE" of the electrode face 105c and the cutting edge of the blade 106c) must seek new pathways through tissue. For example, one current pathway in tissue after the cut may include traveling along and under the newly formed resection line (e.g., current travels along one side of the cut, under the cut line and along the other side of the cut) thereby treating the newly cut tissue. Another current pathway in tissue after the cut may include currents traveling longitudinally toward the leading edge "LE", and around the cutting edge of the blade 106c (through uncut tissue).

As such, the electrosurgical pencil 100, 200 and the bipolar resection apparatus 300 discussed herein provide electrosurgical treatment to the tissue along the resection line before and after the tissue is cut by the blade 106c.

The current pathway through cut tissue, between the first bipolar electrode 158a and the second bipolar electrode 158b (e.g., the tissue along the resection line that has been cut by the cutting edge of blade 106c) are longer (e.g., in distance) than the current pathways through uncut tissue. For example, current pathways through uncut tissue are typically along the surface tissue and the length of the pathways are about equal to the transverse distance between the first and second bipolar electrodes 158a, 158b. The blade 106a severs the surface tissue along the resection line and new current pathway form along and/or under the resection line. For example, one new current pathway may be formed along the newly cut tissue with the distance of the current pathway equal to the depth of the cut along a first side of the resection line, the distance along the second side of the resection line and the distance between the first and second bipolar electrodes 158a, 158b.

To compensate for the increase in the overall length of the current pathway through tissue after the blade 106c cuts the tissue along the resection line, the surface area of the first and second bipolar electrodes 158a, 158b between the trailing edge "TE" and the cutting edge of the blade 106c increases and the transverse distance between the first and second bipolar electrodes 158a, 158b decreases. As such, the increase in the length (e.g., distance) of the tissue pathway due to the cut formed in the tissue is at least partially offset by the surface area increase and/or the decrease of the transverse distance between the first and second bipolar electrodes 158a, 158b.

FIG. 8B illustrates a structurally similar arrangement on the electrode face 105d as the electrode face 105c illustrated in FIG. 8A and described hereinabove. While the structural arrangement may be similar, the electrical connections are different. In FIG. 8B, the electrode face 105b includes a pair of similarly polarized electrodes 168a and a blade 106d, wherein at least a portion of the blade 106d forms the opposing polarized electrode. As illustrated in FIG. 8B and described herein, the entire blade 106d forms the first electrode. In this particular embodiment, all current pathways in tissue are formed between the blade 106d formed as one electrode and one or both of the first bipolar electrodes 168a.

In this particular embodiment, the current density is greatest in tissue adjacent the blade 106d. In particular, the current density in tissue may be concentrated along the portion of the blade 106d where the contact quality with tissue is greatest, such as, for example, the cutting edge of the blade 106d and/or a portion of the blade 106d adjacent a maximum transverse width.

Any tissue not fully treated prior to the cut will be coagulated and/or cauterized as the blade 106d passes in direction "DD" through the tissue. Similarly, fluid released from tissue during the cut may contact the blade 106d thereby improving the contact quality between the blade 106d and tissue thereby promoting tissue treatment at the point of fluid release.

Figure 9:
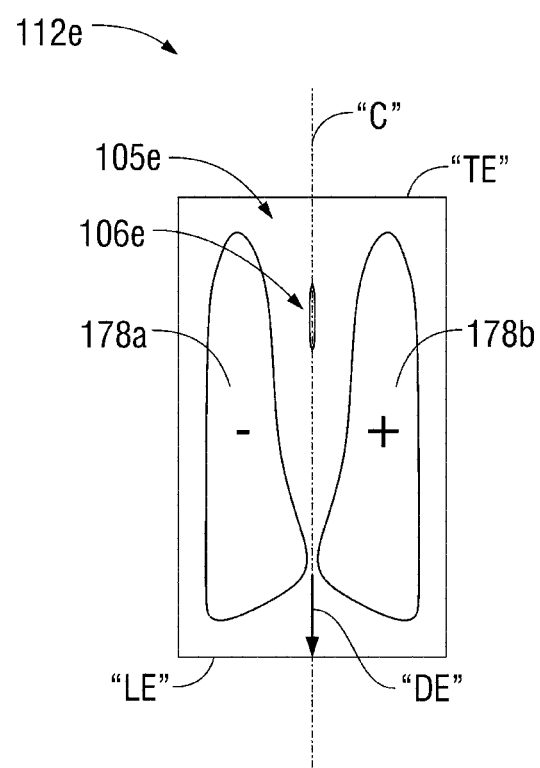
FIG. 9 is a bottom view of an electrode body including a unidirectional electrode face, in accordance with another embodiment of the present disclosure.

FIG. 9 is a bottom view of an electrode body 112e illustrating an electrode face 105e with a unidirectional bipolar electrode arrangement. Electrode face 105e includes a first bipolar electrode 178a, a second bipolar electrode 178b and a blade 106e. First bipolar electrode 178a and second bipolar electrode 178b are substantially symmetric with respect to each other about the longitudinal centerline "C". Blade 106e is positioned adjacent the trailing edge "TE" of the electrode face 105e (i.e., away from the direction of travel "DE") and between the first and second bipolar electrodes 178a and 178b. The transverse distance between the first bipolar electrode 178a and the second bipolar electrode 178b is at a minimum adjacent the leading edge "LE" thereby generating a high current density in tissue positioned therebetween. Moving longitudinally toward the trailing edge "TE", the transverse distance between the first and second bipolar electrodes 178a, 178b gradually increases to a maximum cross-directional distance therebetween near the trailing edge "TE".

In use, while the configuration of the first and second bipolar electrodes 178a and 178b may be configured to deliver a majority of the electrosurgical treatment to uncut tissue positioned forward the cutting edge of the blade 106e, a portion of electrosurgical treatment is still provided to the cut tissue along the resection line (i.e., treating tissue after the cut).

Figure 10A:
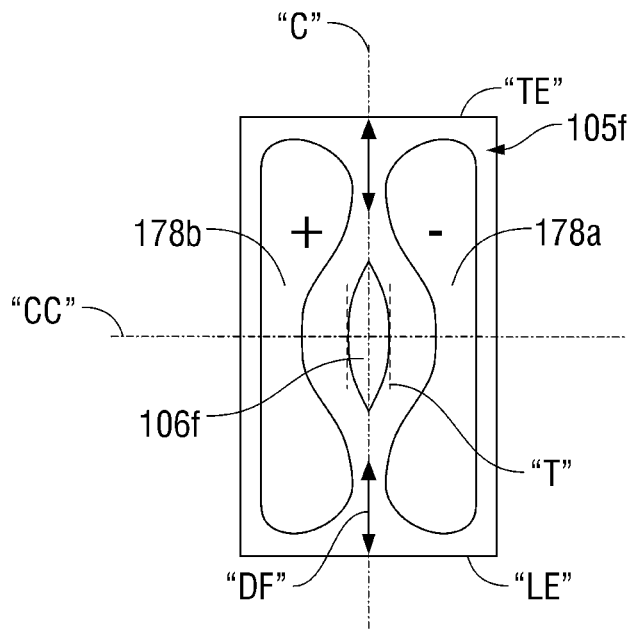
FIG. 10A is a bottom view of an electrode body including a substantially symmetric bidirectional electrode face, in accordance with another embodiment of the present disclosure.
Figure 10B:
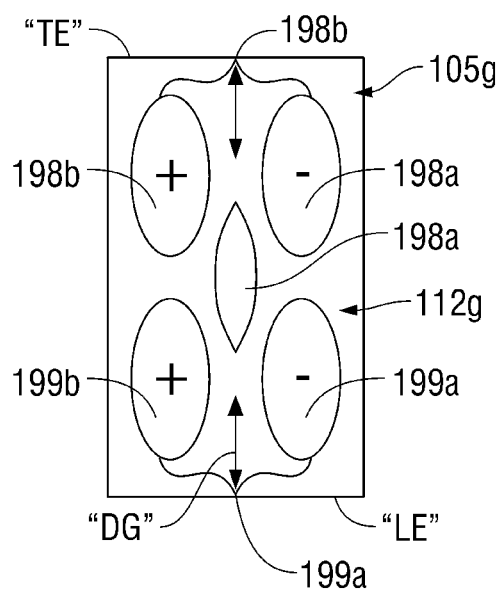
FIG. 10B is a bottom view of an electrode body including an electrode body with two pairs of bipolar electrodes, in accordance with another embodiment of the present disclosure.

FIGS. 10A and 10B are bottom views of electrode bodies 112f, 112g illustrating electrode faces 105f, 105g, respectively, with bidirectional bipolar arrangements. FIG. 10A includes an electrode face 105f, similar to the electrode face 105b illustrated in FIG. 7B, including a blade 106f with bidirectional cutting surfaces. Blade 106f is configured to cut in a first direction with a first blade cutting edge and cut in a second direction with a second blade cutting edge. Blade 106f further includes arcuate longitudinal side edges and a maximum thickness "T". First bipolar electrode 188a and second bipolar electrode 188b are substantially symmetric with respect to each other about the longitudinal centerline "C" and symmetric with respect to each other about the transverse line "CC". The bidirectional bipolar arrangements may be drawn across tissue in a first direction to cut tissue and drawn across tissue in a second direction, oppose the first direction, to focus current flow along the walls of the cut tissue to coagulate tissue and/or to stop bleeding, as discussed hereinabove.

FIG. 10B includes an electrode face 105g of an electrode body 112g including a blade 106g with bidirectional cutting surfaces, a trailing bipolar electrode pair 198 and a leading bipolar electrode pair 199. Trailing bipolar electrode pair 198 includes a trailing first bipolar electrode 198a and a trailing second bipolar electrode 198b. Leading bipolar electrode pair 199 includes a leading first bipolar electrode 199a and a leading second bipolar electrode 199b. Trailing bipolar electrode pair 198 and leading bipolar electrode pair 199 may be electrically connected and configured to receive an electrosurgical signal from the same source and together may operate in a substantially similar manor to the electrode bodies 112, 112a-112g including one bipolar electrode pair, as described herein.

In another embodiment, the trailing bipolar electrode pair 198 and the leading bipolar electrode pair 199 are configured to receive independently controlled electrosurgical signals therebetween. In one embodiment, the electrosurgical generator "G" (See FIG. 1) provides a first electrosurgical signal between the trailing bipolar electrode pair 198 and a second electrosurgical signal between the leading bipolar electrode pair 199. First and second electrosurgical signals may be a single electrosurgical signal time-proportioned between the trailing bipolar electrode pair 198 and the leading bipolar electrode pair 199. Alternatively, the first and second electrosurgical signals may include two separate electrosurgical signals provided to each bipolar electrode pair 198, 199. Generator "G" may be configured to provide the first and the second electrosurgical signals or electrosurgical signals may be provided by a first and a second generator functioning independently or in conjunction with each other.

Additional conductors may be required to provide a second electrosurgical signal. For example connecting wire, the plug assembly 400, 424, electrosurgical pencil 100, shaft 110 and electrode body 112 may require one or more additional conductors for the second electrosurgical signal supplied the electrode face 105g. In one embodiment, the first and second electrosurgical signals are provided via a three-conductor triaxial cable.

In another embodiment, the generator "G" (See FIG. 1) is configured to selectively apply an electrosurgical signal between any two of the bipolar electrodes 198a, 198b, 199a, 199b. For example, generator "G" may time-proportion the bipolar electrosurgical signal across either of the bipolar electrode pairs 198, 199 for a first period of time and then supply the electrosurgical signal between any two of the four electrodes 198a, 198b, 199a, 199b for a second period of time.

The electrosurgical pencils 100, 200 and the bipolar resection device 300, described and illustrated herein, are configured to coagulate and/or cauterize tissue along a resection line, before and/or after the resection. Embodiments described herein are configured to compensate for uncontrollable and varying operating parameters that occur due to a clinician's individual style or techniques. In the context of this application, an "uncontrollable and varying operating parameter" (hereinafter "uncontrollable parameter") is defined as an operating condition that varies due to an action of a clinician.

Two such uncontrollable parameters include the velocity and downward force applied by the clinician as an electrosurgical pencil 100, 200 is drawn along a resection line. These uncontrollable parameters, velocity and downward force, often vary during a procedure and/or between two separate procedures.

The electrosurgical pencil 100, 200 described herein provides consistent operation over a wide range of uncontrollable parameters. With respect to a varying velocity, the electrosurgical pencil 100 is configured to treat tissue before and/or after the cut. An electrosurgical pencil 100 according to one embodiment of the present disclosure is drawn across tissue along a resection line at a first velocity and subsequently drawn along a second resection line (and through substantially similar tissue) at a second velocity, wherein the second velocity is greater than the first velocity. At the first velocity, ninety percent of tissue treatment occurs prior to the cut and the remaining ten percent occurs after the cut. At the second velocity, seventy percent of tissue treatment occurs prior to the cut and the remaining thirty percent occurs after the cut. As such, the electrosurgical pencil 100 provides a sufficient amount of treatment at each velocity by varying the ratio of the treatment provided before the resection and after the resection. An accelerometer may be employed to compute, control or correct the amount of electrosurgical energy provided to the bipolar electrodes as a function of the velocity or acceleration of the treatment. Electrosurgical pencil 100, 200 may also include drag sensing capability as recited in commonly-owned U.S. Pat. No. 7,393,354 to Buchman et al. incorporated herein in its entirety by reference.

Drag sensing capability may be used to determine the speed or direction of travel and provide feedback to adjust one or more parameters related to energy delivery or blade position. Energy delivery may be adjusted to provide a desirable ratio between energy delivered to tissue in front of the blade and energy delivered to tissue behind the blade and/or a dynamic adjustment may be made to the position/direction of the blade.

With respect to the amount of downward force applied by the clinician, increasing the down downward force may increase the depth of the resection. As discussed hereinabove, if tissue along the resection line is untreated or under-treated prior to the cut, the untreated or under-treated tissue receives further treatment after the cut. A pressure sensor may be employed to compute, control or correct the amount of electrosurgical energy provided to the bipolar electrodes as a function of the pressure applied by the clinician and/or the pressure measured by the pressure sensor.

Figure 11A:
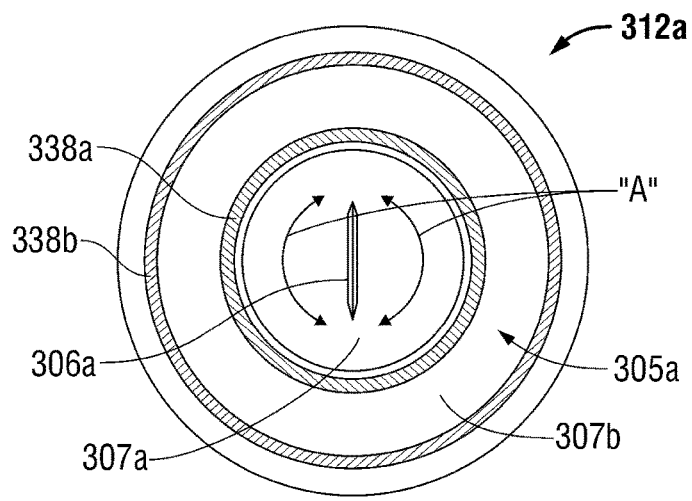
FIG. 11A is a bottom view of a generally cylindrical electrode body including concentric bipolar electrodes with a multi-directional blade and blade housing assembly.
Figure 11B:
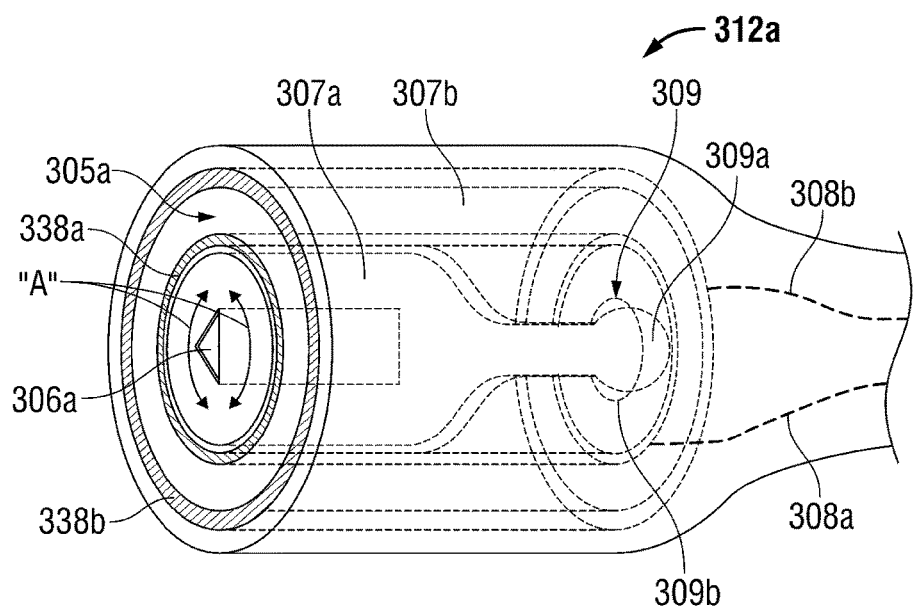
FIG. 11B is a perspective view of the generally cylindrical electrode body of FIG. 11A illustrating one embodiment of a multi-directional blade and blade housing assembly.

FIGS. 11A-11F are various views of generally cylindrical electrode bodies 312a, 312c-312f, including circular electrode faces 305a, 305c-305f with multi-directional bipolar arrangements. FIG. 11A is a bottom view and FIG. 11B is a perspective view of a generally cylindrical electrode body 312a including a blade 306a with bidirectional cutting surfaces, a first bipolar electrode 338a concentrically-disposed about the blade 306a and a second bipolar electrode 338b concentrically-disposed about the first bipolar electrode 338a. Blade 306a and rotating blade housing 307a are configured to rotate with respect to the first bipolar electrode 338a, the second bipolar electrode and/or the shaft 308, as indicated by arrows "A". First bipolar electrode 338a and second bipolar electrode 338b are separated by a dielectric spacer 307b that insulates and/or separates the first bipolar electrode 338a and the second bipolar electrode 338b.

Proximal end of rotating blade housing 307a forms a ball 309a of a ball-and-socket joint 309. Ball 309a mates with socket 309b and is configured to rotate freely in socket 309b as indicated by arrows "A". Ball-and-socket joint 309 is configured to allow the rotating blade housing 307a to rotate with respect to the remaining portion of the electrode body 312a.

Ball-and-socket joint 309 may include fluid that provides lubrication between the ball 309a and socket 309b. A seal may prevent the lubricating fluid from flowing from the ball-and-socket joint 309 to the electrode face 305a. Fluid may be compatible with the surgical site and flow distally through the electrode body 312a thereby lubricating the interface between the rotating blade housing 307a and the remaining portion of the electrode body 312a.

While a ball-and-socket joint 309 is described herein and illustrated in the Figures, other suitable means may be used to provide rotation between the rotating blade housing and the remaining portion of the electrode body 312a. For example, roller bearings, ball thrust bearings or roller thrust bearings may be mounted on the proximal end of the rotating blade housing 307a or a ball bearing assembly may be mounted on the side of the rotating blade housing 307a.

First bipolar electrode 338a connects to a first electrical conductor 308a and the second bipolar electrode 338b connects to a second electrical conductor 308b. First bipolar electrode 338a and second bipolar electrode 338b may be positioned coaxially within the electrode body 312a, as illustrated in FIG. 11B, or electrodes 338a, 338b may be concentrically-formed on the electrode face 305a. When activated, first and second electrical conductors 308a, 308b provide an electrosurgical energy signal to the first and second bipolar electrodes 338a, 338b thereby providing an opposed, electrical potential therebetween.

In one embodiment, the rotational position of the blade 306a and the rotating blade housing 307a, with respect to the electrode body 312a and shaft 308, is controlled by the direction of travel of the electrode body 312a (e.g., the path in which the electrode body 312a is drawn across patient tissue). After the blade 306a is positioned in patient tissue, the position of the blade 306a is controlled by the tissue pathway and any change in direction of the electrode body 312a causes the blade 306a and electrode body 312a to rotate about the ball-and-socket joint 309 thus changing position with the direction of the electrode body 312a. As such, the position of the blade 306a remains substantial parallel to the path of the electrode body 312a as the electrode body 312 is drawn across tissue.

Figure 11C:
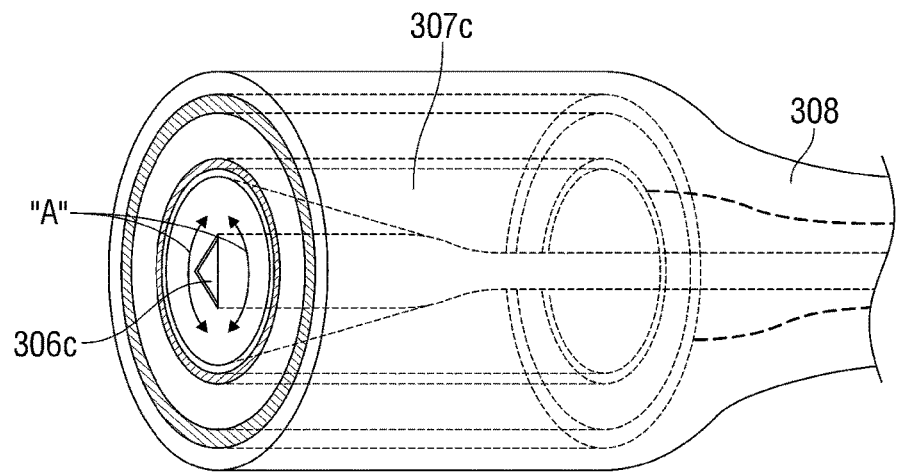
FIG. 11C is a perspective view of another embodiment of the generally cylindrical electrode body of FIG. 11A illustrating an alternative arrangement for the multi-directional blade and blade housing assembly.

FIG. 11C is a perspective view of an alternative arrangement of the cylindrical electrode body 312a of FIG. 11A. Proximal end of the rotating blade housing 307a extends proximally through the shaft 308 and connects to a rotational member on the elongated housing (not explicitly shown; see roll controller 262, FIGS. 12 and 14; elongated housing 102, FIG. 1). Rotational member varies the position of the blade 306c and rotating blade housing 307a with respect to the shaft 308 and elongated housing. A clinician may actively effectuate the rotational member during a resection procedure and dynamically adjust the position of the blade 306c and rotating blade housing 307a with respect to the remaining portions of the electrode body 312c.

Figure 11D:
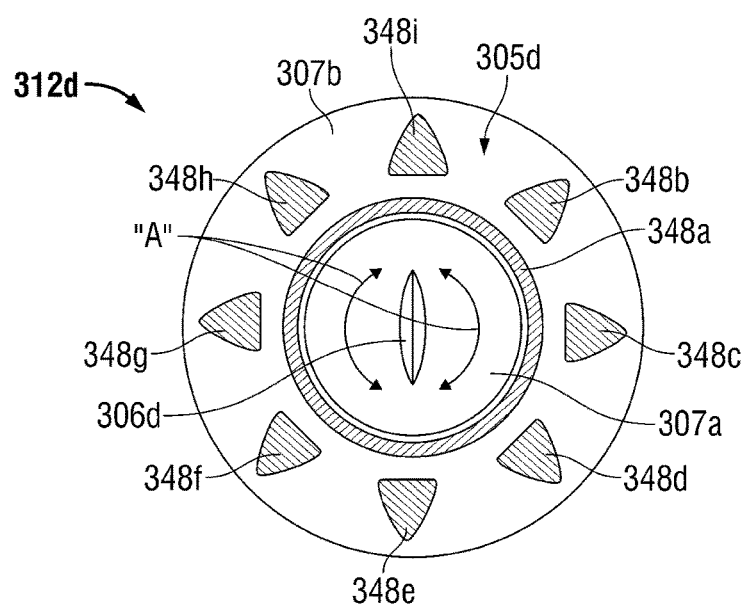
FIG. 11D is a bottom view of another embodiment of a generally cylindrical electrode body including a concentric first bipolar electrode and a plurality of second bipolar electrodes spaced radially outwardly from the first bipolar electrode, concentrically arranged and evenly spaced.

FIG. 11D is another embodiment of a generally cylindrical electrode body 312d forming a circular electrode face 305d that includes a blade 306d with bi-directional cutting surfaces, a first bipolar electrode 348a concentrically-disposed about the blade and a plurality of second bipolar electrode 348b-348i concentrically-disposed about the first bipolar electrode 384a. The second bipolar electrodes 348b-348i are spaced radially outward from the first bipolar electrode 348a, concentrically arranged and evenly spaced about the first bipolar electrode 348a, blade 306d and rotating blade housing 307a. Blade 306d and rotating blade housing 307a are configured to rotate with respect to the first bipolar electrode 348a, the plurality of second bipolar electrodes 348b-348i and/or the shaft 308, as illustrated by arrows "AA" (See FIGS. 11B and 11C discussed hereinabove).

Dielectric spacer 307b forms a plurality of electrode apertures 349b-349i that each house a respective one of the plurality of second bipolar electrodes 348b-348i. Dielectric spacer 307b also insulates and/or separates the first bipolar electrode 338a from each of the plurality of second bipolar electrode 348b-348i. The plurality of second bipolar electrodes 348b-348i connect to the source of electrosurgical energy thereby generating an electrical potential between the first bipolar electrode 348a and each of the plurality of second bipolar electrodes 348b-348i.

Figure 11E:
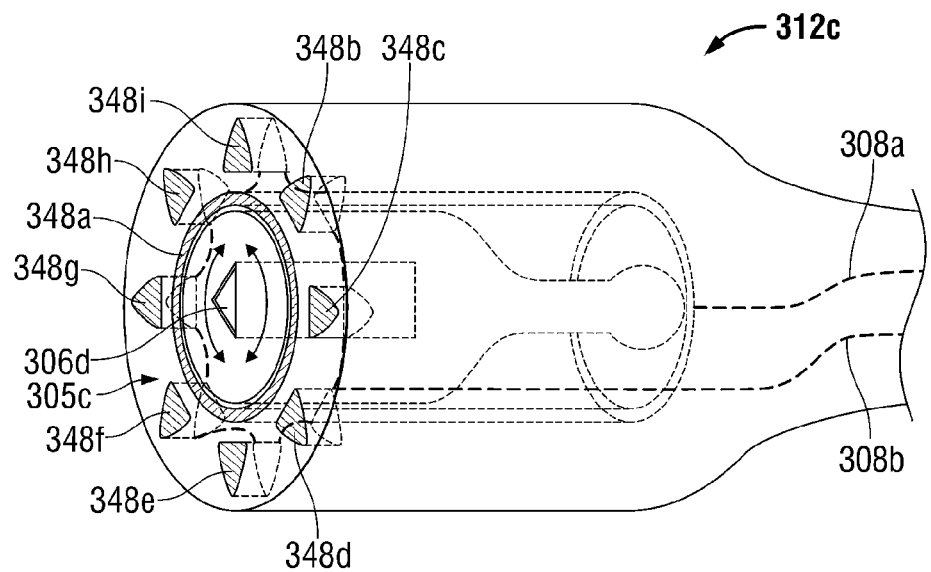
FIG. 11E is a perspective view of the cylindrical electrode body of FIG. 11D illustrating each of the plurality of second bipolar electrodes electrically connected to a contact ring.

FIG. 11E is a perspective view of the cylindrical electrode body 312d of FIG. 11D illustrating the first bipolar electrode 348a connected to the first electrical conductor 308a and each of the plurality of second bipolar electrodes 348b-348i electrically connected to the second electrical conductors 308a. The first electrical connector 308a may connect directly to one or more electrodes (e.g., electrode 348d) and connect indirectly to the remaining second bipolar electrodes 348b-348c, 348e-348i (e.g., via a plurality of electrical jumpers as illustrated in FIG. 11E). Any suitable connector arrangement may be used to electrically connect the source of electrosurgical energy to the electrodes, such as, for example, a circular contact ring. In another embodiment, the plurality of second bipolar electrodes are formed from a single electrode body that includes a plurality of posts that extend through the electrode body 312e and to the electrode face 305e.

When activated, first electrical conductor 308a and the second electrical conductor 308b provide an electrosurgical energy signal between the first bipolar electrode 348a and the plurality of second bipolar electrodes 348b-348i, respectively, thereby producing electrical potentials between the first bipolar electrode 348a and each of the plurality of second bipolar electrodes 348b-348i. Blade 306d and rotating blade housing 307d are configured to rotate with respect to the first bipolar electrode 348a and the plurality of second bipolar electrodes 348b-348i as illustrated in FIGS. 11B and 11C, discussed hereinabove.

Figure 11F:
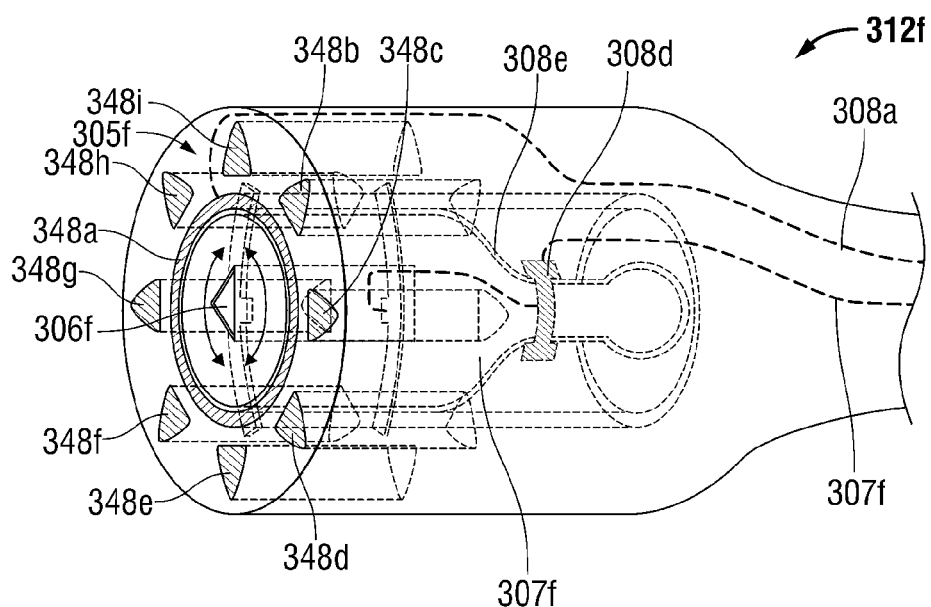
FIG. 11F is a perspective view of a cylindrical electrode body of FIG. 11D configured to selectively connect two or more second bipolar electrodes to a source of electrosurgical energy.

In another embodiment, at least two of the second bipolar electrodes 348b-348i are selectively connected to the second electrical conductor 308b. The selected bipolar electrodes 348b-348i that connect to the second electrical conductor 308b may be determined by the position of the blade 306a, the direction of travel and/or an applied forced (e.g., a force applied to the electrosurgical instrument). For example, as illustrated in FIG. 11F, the cylindrical electrode body 312f is configured to selectively connect two or more of the bipolar electrodes 348b-348i to the second connector 308b based on the position of the blade 306f. The first electrical connector 308a connects to the first bipolar electrode 348a. The second electrical connector 308b forms an electrical connection to the rotating blade housing 307f through a slip connector 308d connected between the rotating blade housing 307f and the electrode body 312f. Slip connector 308d may include a rotary electrical interference connector, a rotating electrical connector, a collector, a swivel, an electrical rotary joint or any other suitable connector capable of making an electrical connection through a rotating assembly.

Figure 11G:
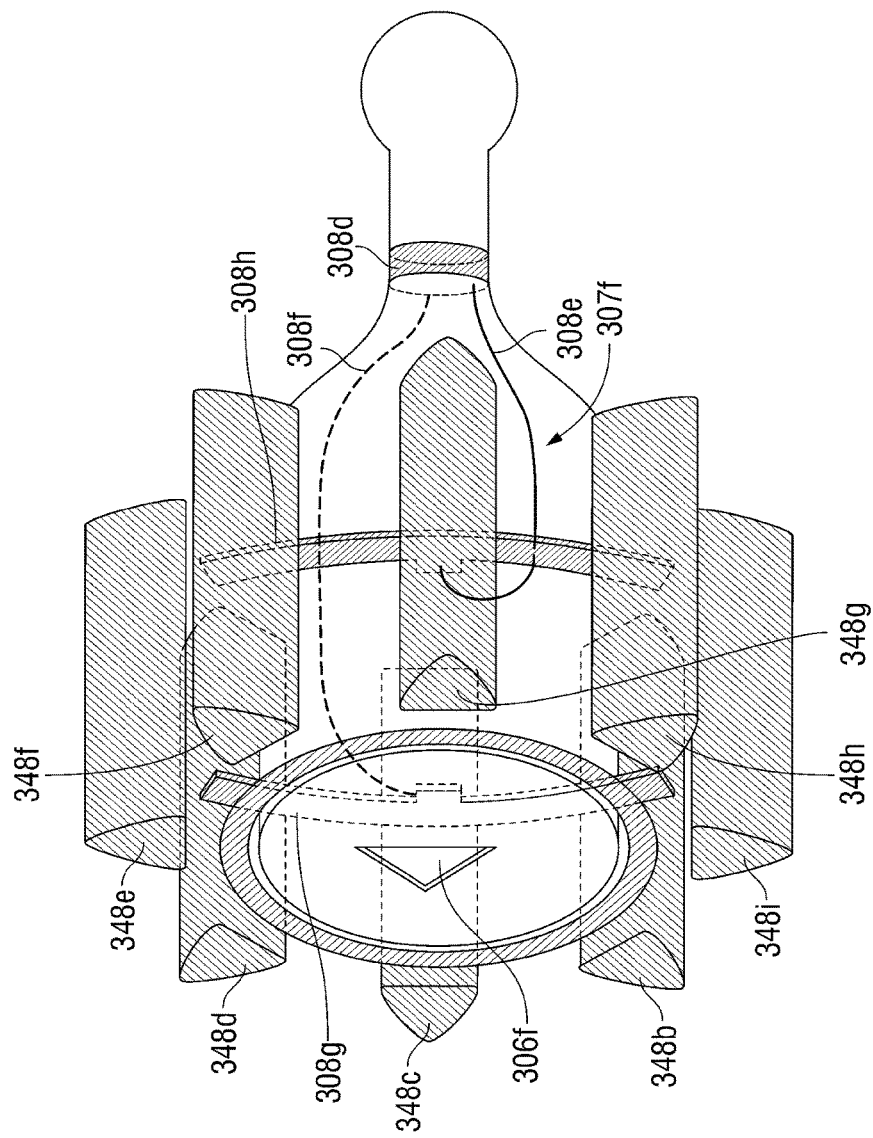
FIG. 11G is a perspective view of a portion of the cylindrical electrode body of FIG. 11F.

The first slip connector 308d connects to first and second electrical traces 308e, 308f formed on, or in, the rotating blade housing 307f. First and second electrical traces 308e, 308f electrically connect to first and second electrode selectors 308g, 308h, respectively. The first and second electrode selectors 308g, 308h are attached on opposite sides of the rotating blade housing 307f and each form an electrical connection with one or more of the second bipolar electrodes 348b-348i. As illustrated in FIG. 11G, the selected second bipolar electrodes (e.g. second bipolar electrodes 348b-348d selected by first electrode selector 308g and second bipolar electrodes 348f-348h selected by second electrode selector 308h) may be positioned on each side of the blade 305f although any suitable arrangement may determine the position and circumferential length of the first and second electrode selectors 308g, 308h.

In another embodiment, the electrode body may include a unidirectional blade (e.g., See FIGS. 8A and 8B with unidirectional electrode bodies) and the position of the first and second electrode selectors is shifted toward the intended direction of travel.

FIG. 11G is a partial perspective view of the electrode body of FIG. 11 that illustrates the interconnections between the slip ring 308d, the first and second electrical traces 308e, 308f, the first and second electrode selectors 308g, 308h and the plurality of second bipolar electrodes 348b-348i. On one side of the blade 306f the first electrode selector 308g contacts three bipolar electrodes 348b-348d. On the opposite side of the blade 306f the second electrode selector 308h contacts another three bipolar electrodes 348f-348h. The position of the selected second bipolar electrodes is determined by the position of the first and second electrode selectors 308g, 308h and the position of the blade 306f.

The number and position of the first bipolar electrode 348a and second bipolar electrodes 348b-348i and the number and circumferential length of the electrode selectors 308g, 308h is a matter of design selection and may vary depending on the particular electrode body and/or the intended use thereof.

Figure 12:
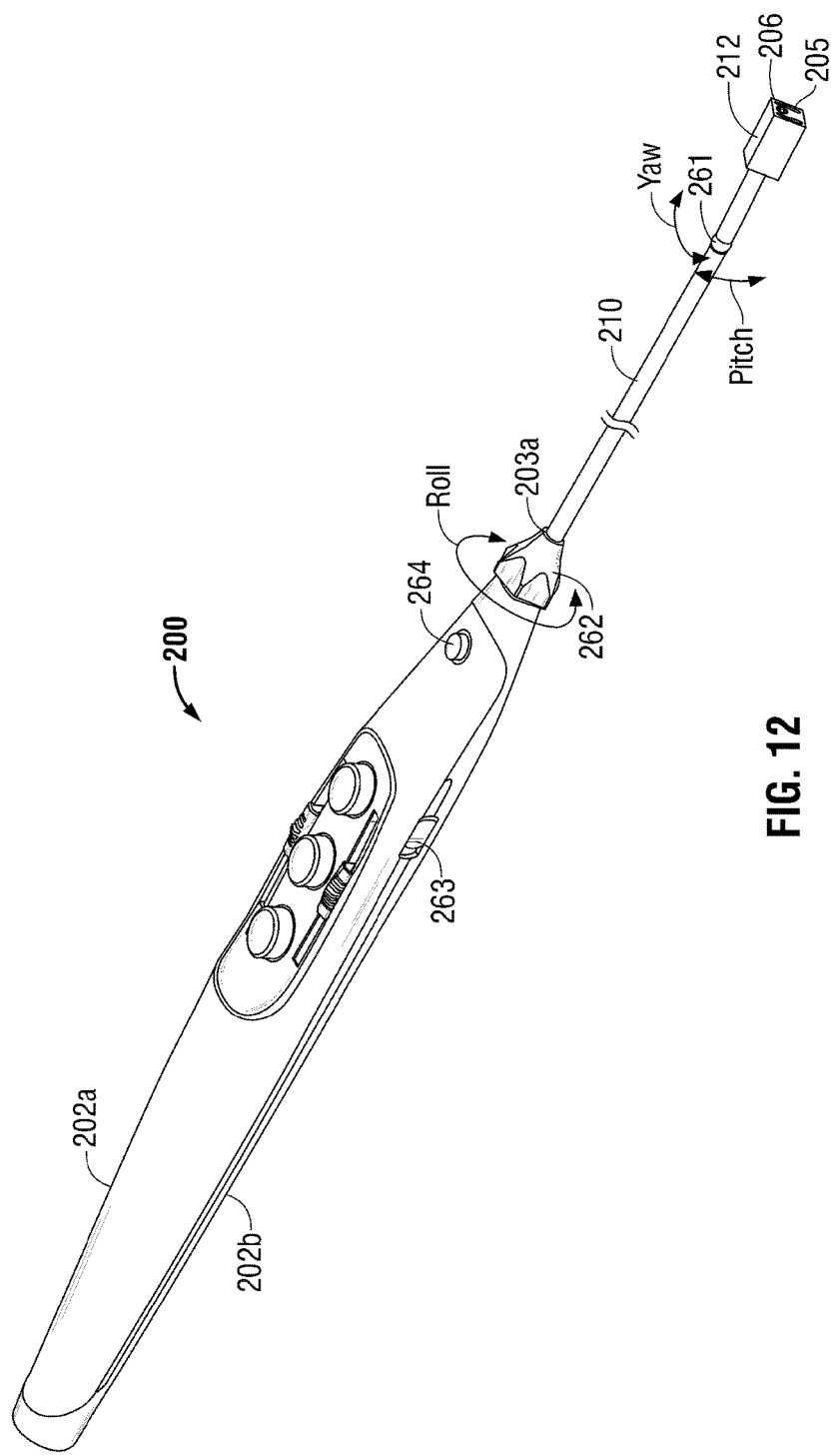
FIG. 12 is a perspective view of an electrosurgical pencil with an articulating electrode body in accordance with another embodiment of the present disclosure.

Turning now to FIG. 12, an electrosurgical pencil 200 according to another embodiment of the present disclosure includes an articulating electrode body 212. The electrosurgical pencil 200 is similar to the electrosurgical pencil 100 discussed and illustrated herein and is discussed in detail to the extent necessary to identify differences in construction and operation therein. Electrosurgical pencil 200 includes control mechanisms 262, 263, 264 to effectuate "Roll", "Yaw" and "Pitch", respectively, of the articulating electrode body 212. Roll controller 262 effectuates "Roll" of the shaft 210 and the articulating electrode body 212 connected thereto. Yaw controller 263 and pitch controller 264 are connected to and actuate the wrist joint 261 to effectuate "Yaw" and "Pitch", respectively. Control of "Roll", "Yaw" and "Pitch" may be used to position the electrode face 205 with respect to the target tissue.

The articulating electrode body 212 may include any of the electrode bodies 112, 112a-112h described herein.

"Roll", "Yaw" and "Pitch" of the articulating electrode body 212 is effectuated by manipulation of the roll controller 262, yaw controller 263 and pitch controller 264, respectively. Roll controller 262 connects to and is positioned between the distal opening 203a of the elongated housing 202 and the shaft 210. Roll controller 262 is configured to provide rotation of the shaft 210 and articulating electrode body 212 with respect to the elongated housing 202.

"Yaw" and "Pitch" of the articulating electrode body 212 is effectuated by wrist joint 261 positioned between the shaft 210 and the articulating electrode body 212. "Yaw" movement of the wrist joint 261 is controlled by yaw controller 263 and "Pitch" movement is controlled by pitch controller 264. Yaw controller 263 and pitch controller 264 are mounted in the elongated housing 202 and connect to the wrist joint 261 through the distal opening 203a of the elongated housing 202 and shaft 210.

Yaw controller 263 is a mechanical slide mounted between the top-half shell portion 202a and the bottom-half shell portion 202b housing. Any suitable mechanical and/or electrical adjustment mechanism may be utilized for the yaw controller 263. Yaw controller 263 is connected to wrist joint 261 by one or more yaw elongated members (not explicitly shown) with sufficient rigidity for repeated bidirectional manipulation of the wrist joint 261. Alternatively, yaw elongated member may include a yaw push cable and a yaw pull cable wherein each cable is configured to effectuate movement in a single direction.

Pitch controller 264 is a mechanical slide mounted in the top-half shell portion 102a of the housing 202. Any suitable mechanical and/or electrical adjustment mechanism may be utilized for the pitch controller 264. Pitch controller 264 is connected to wrist joint 261 by one or more pitch elongated members (not explicitly shown) with sufficient rigidity for bidirectional manipulations of the wrist joint 261. Alternately, pitch elongated member may include a pitch push cable and a pitch pull cable wherein each cable is configured to effectuate movement in a single direction.

Control of "Yaw", "Roll" and "Pitch" is particularly useful when an electrosurgical pencil 200 with an articulating electrode body 212 is utilized in a laparoscopic-type procedure. Articulating electrode body 212, wrist joint 261 and shaft 210 may be an elongated member with a substantially uniform thickness therethrough configured for insertion through an internal body access device (i.e., catheter, endoscope or cannula). In use, manipulation of the articulating electrode body 212 portion is independent of the position of the housing 202.

Figure 13A:
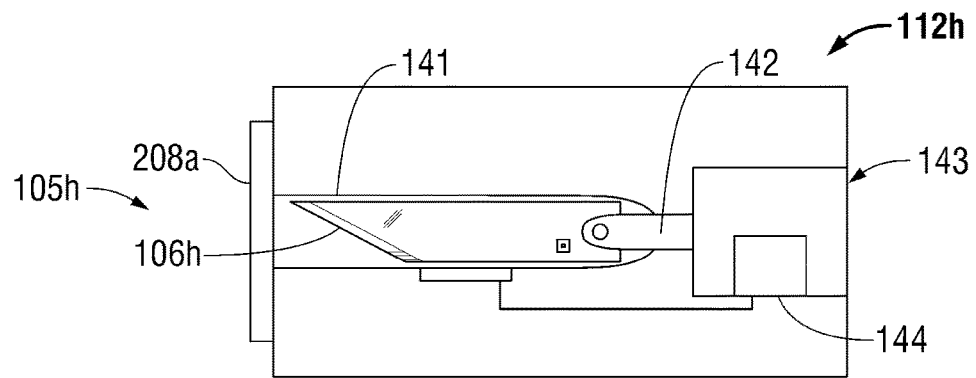
FIG. 13A is a perspective view in partial cross-section of an electrode body with a deployable blade in a first position, in accordance with another embodiment of the present disclosure.
Figure 13B:
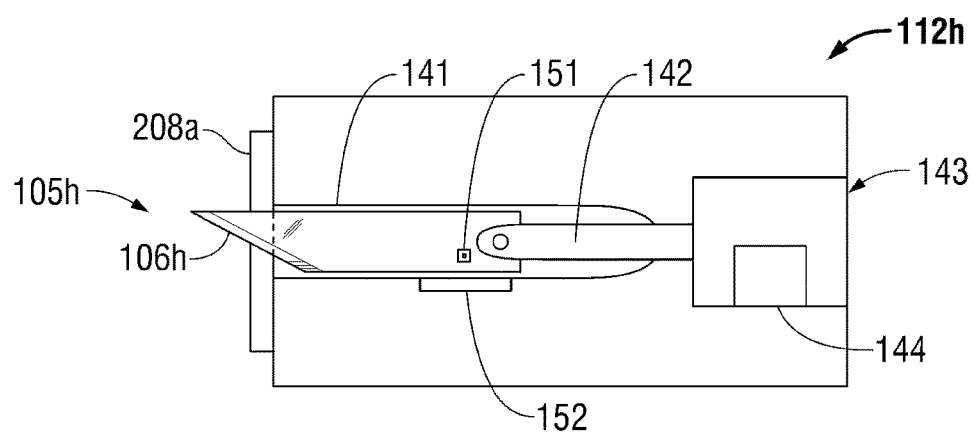
FIG. 13B is a perspective view in partial cross-section of an electrode body of FIG. 13A with the deployable blade in a deployed position.

Turning now to FIGS. 13A and 13B, an electrode body 112h substantially similar to the electrode bodies 112, 112a-112g, discussed and illustrated herein, is shown and will be discussed in detail to the extent necessary to identify difference in construction and operation therein. The construction and operation of electrode body 112*h* may be incorporated into any of the electrode bodies 112, 112*a*-112*g* described herein. Electrode body 112*h* includes a deployable blade 106*h* configured to deploy between a retracted first position, as illustrated if FIG. 13A, and a deployed second position, as illustrated in FIG. 13B. As described herein, a "deployed position" includes all deployable blade 106*h* positions except the retracted first position. The deployed position includes a "fully-deployed position" in which the deployable blade 106*h* is extended to a distal-most position and a plurality of "cut positions", in which the deployable blade 106*h* is capable of cutting tissue.

An electrode body 112*h* including a deployable blade 106*h* provides a clinician the flexibility of using the electrode face 105*h* to coagulate and/or cauterizes without the deployable blade 106*h* being in a cut position. For example, as a pre-treatment to a resection procedure or as a step in a resection procedure, a clinician may retract the deployable blade 106*h* and draw the electrode face 105*h* along the resection line while delivering electrosurgical energy to tissue. Alternatively, during a resection procedure, a clinician may retract the deployable blade 106*h* to a first position, or to a position that is not a cut position, and utilize the electrode face 105*h* to coagulate and/or cauterize under-treated tissue along the resection line.

Electrode body 112*h* including a deployable blade 106*h* may also be utilized by a clinician as a measuring device to measure one or more parameters related to a target tissue. In a selectable mode of operation, the first and second bipolar electrodes 208*a*, 208*b* are utilized by the generator "G" (See FIG. 1) as sensors and the generator "G" measures one or more properties related to the tissue. For example, with the deployable blade 106*h* not in a cut position, the clinician may draw the electrode face 105*h* along a resection line and measure one or more tissue properties. For example, generator "G" may measure tissue impedance along the resection line and indicate the presence (or lack thereof) of vessels and/or arteries, fluid pockets, and/or tissue with one or more properties not in conformity with the target tissue.

Deployable blade 106*h* slideably engages a guide slot 141 defined in the electrode body 112*h*. Guide slot 141 may also be a tubular member housed in a cavity defined in the electrode body 112*h* wherein internal shape and dimensions of the tubular member are configured to accommodate the shape and dimensions of the deployable blade 106*h* (i.e., a single cutting edge, a dual cutting edge and/or the width and shape thereof). The deployable blade 106*h* connects to a piston 142 actuated by an actuator 143. The actuator 143 is configured to actuate the piston 142 to two or more positions, wherein the two or more positions include a first, retracted position and at least one cut position.

In another embodiment, the actuator 143 may be configured to selectively control the position of the deployable blade 106*h*. Actuator 143 may include a position control system to dynamically measure and control the position of the piston 142. Alternatively, deployable blade 106*h* may include a marker 151 that is measured by a position sensor 152. Position sensor 152 provides a position signal related to the position of the marker to controller 144. Controller 144 drives the actuator 143 and controls the position of the piston 142. Position sensor 152 may also be configured to sense a portion of the deployable blade 106*h*, such as, for example, the distal sharpened tip or the proximal end portion. Controller 144 may be positioned in the electrode body 112*h*, as illustrated in FIGS. 13A, 13B or controller 144 may be incorporated into the elongated housing 102 or the generator "G" (see FIGS. 1 and 2).

Figure 14:
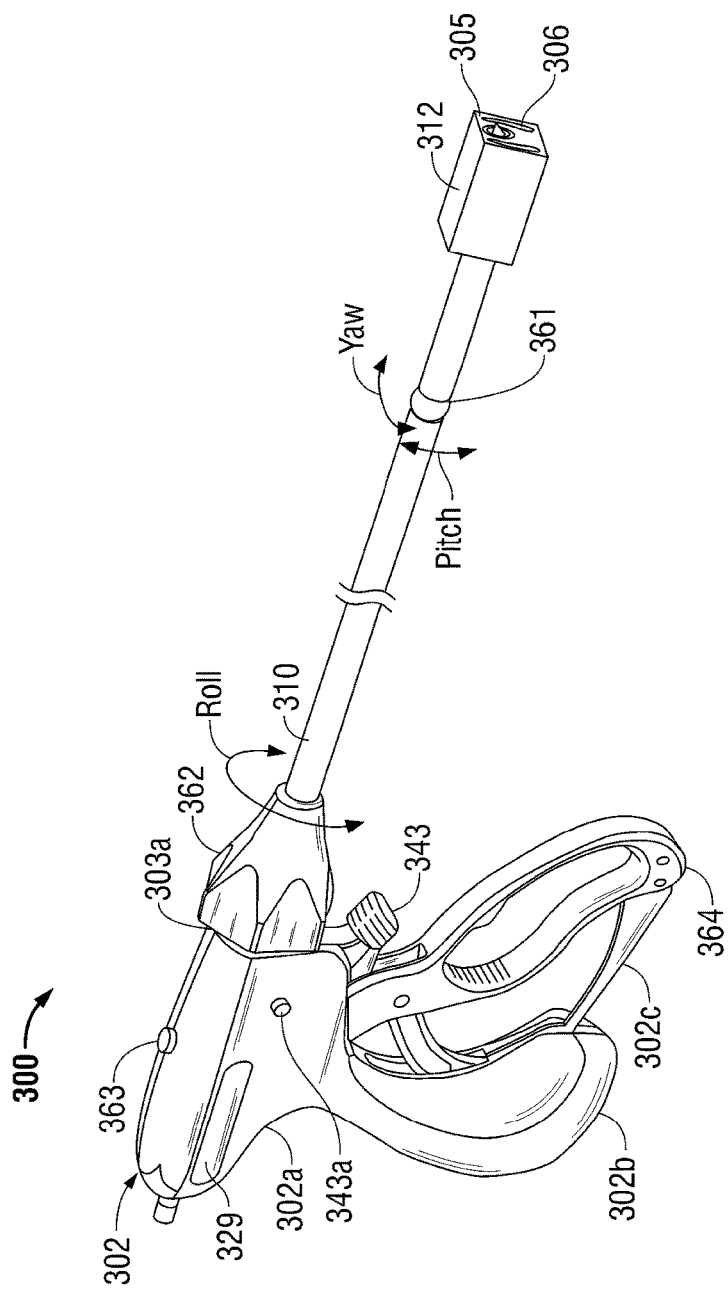
FIG. 14 is a perspective view of a multi-functional bipolar resection apparatus with an articulating electrode body including a deployable blade, in accordance with another embodiment of the present disclosure.

Turning now to FIG. 14, a bipolar resection apparatus, including functionality similar to the electrosurgical pencils 100, 200 discussed and illustrated herein, is shown as 300 and will be discussed in detail to the extent necessary to identify differences in construction and operation therein. Bipolar resection apparatus 300 includes a housing 302 connected to an articulating electrode body 312 through a roll controller 362, shaft 310 and elbow joint 361. The articulating electrode body 312 further includes a deployable blade 306. Bipolar resection apparatus 300 incorporates an articulating electrode body 312 and deployable blade 306, similar to deployable blade 106*h* and electrode body 212 illustrated in FIGS. 12, 13A and 13B, respectively, as discussed hereinabove.

Housing 302 includes a body 302*a* and a handle 302*b*. Handle 302*b* includes grip 302*c*, pitch controller arm 364 and blade trigger 343. Grip 302*c* is configured to conform to a clinician's hand to facilitate one-handed operation, one-handed manipulation of the articulating electrode body 312 and/or one-handed manipulation of the deployable blade 306. Pitch controller arm 364 is configured to control the "Pitch" of the articulating electrode body 312 with respect to the shaft 310. Blade trigger 343 is configured to manipulate the deployable blade 306 housed within the articulating electrode body 312. Blade lock 343*a*, housed in the body 302*a* is configured to lock the position of the blade trigger 343 (and the position of the deployable blade 306) at a desirable position to prevent inadvertent movement or undesirable adjustments of the deployable blade 306 with respect to the electrode face 305.

Yaw controller 363, power controller 329 and blade lock 343*a* are housed in body 302*a*. Yaw controller 363 is configured to control the "Yaw" of the articulating electrode body 312 with respect to the shaft 310. Power controller 329 controls the power output of the first and second bipolar electrodes (not explicitly shown) on the electrode face 305.

Roll controller 362 is mounted between the distal opening 303*a* of body 302*a* and shaft 310. Roll controller 362 is configured to provide rotational movement of the shaft 310 with respect to the housing 302.

The various control mechanisms for controlling "Yaw", "Roll" and "Pitch" are known in the art and may include a series of cables, actuators, gears, drive rods, and other mechanical and/or electro-mechanical components.

The electrosurgical instruments disclosed herein may utilize any of the electrode bodies 112*a*-112*h* or any combination of features described herein.

The electrosurgical pencils 100, 200 and bipolar resection apparatus 300 may include smart recognition technology which communicates with the generator to identify the device, the electrode body 112, 112*a*-112*h*, and/or one or more parameters associated with the devices or a parameter, 212. The identity and/or any surgical parameters recognized by the smart recognition technology that relate to treating tissue are communicated to the generator "G". For example, an electrosurgical pencil 100 may be equipped with a bar code or Aztec code readable by the generator "G". The generator "G" may select presets and/or default parameters associated with treating tissue with the identified device. The bar code or Aztec code may also include programmable data which is readable by the generator and which programs the generator to specific electrical parameters prior to use.

Other smart recognition technology is also envisioned which enables the generator to determine the type of instrument being utilized or to insure proper attachment of the instrument to the generator as a safety mechanism. One such safety connector is identified in U.S. patent application Ser. No. 10/718,114, filed Nov. 20, 2003. For example, in addition to the smart recognition technology described above, such a safety connector can include a plug or male portion operatively associated with an electrosurgical pencil 100, 200 or a bipolar resection apparatus 300 and a complementary socket or female portion operatively associated with the electrosurgical generator.

Although the subject apparatuses has been described with respect to the described embodiments, it will be readily apparent, to those having ordinary skill in the art to which it appertains, that changes and modifications may be made thereto without departing from the spirit or scope of the subject apparatuses.

What is claimed is:

1. An electrosurgical instrument, comprising:
   a housing defining a longitudinal axis; and
   an electrode body coupled to the housing, the electrode body comprising:
      an electrode face formed on a distal-most end of the electrode body, wherein the entire electrode face defines a plane that is perpendicular to the longitudinal axis;
      a rotatable blade housing defining an opening;
      a blade longitudinally moveable with respect to the rotatable blade housing while the electrode body is treating tissue and configured to extend through the opening to dispose at least a portion of the blade distally beyond the electrode face;
      a first electrode disposed concentrically about the opening; and
      a second electrode disposed concentrically about the first electrode, the blade configured to rotate relative to the first and second electrodes.

2. The electrosurgical instrument according to claim 1, wherein the first and second electrodes are configured to connect to opposite electrical potentials of an electrosurgical energy source.

3. The electrosurgical instrument according to claim 1, wherein the blade includes a bidirectional cutting surface.

4. The electrosurgical instrument according to claim 1, wherein the blade is configured to rotate relative to the electrode body while the electrode body is treating tissue.

5. The electrosurgical instrument according to claim 1, wherein the electrode body is cylindrically shaped.

6. The electrosurgical instrument according to claim 1, wherein the blade is configured to move longitudinally with respect to the rotatable blade housing between an undeployed position, wherein a distal end of the blade is disposed proximal to the electrode face, and a plurality of deployed positions, wherein at least a portion of the blade is disposed distally beyond the electrode face.

7. The electrosurgical instrument according to claim 6, further comprising an actuator operably coupled to the blade and configured to move the blade between the undeployed position and the plurality of deployed positions.

8. The electrosurgical instrument according to claim 1, further comprising at least one actuator configured to move the electrode body in at least one of a yaw direction, a pitch direction, and a rotation direction relative to the longitudinal axis.

9. The electrosurgical instrument according to claim 1, wherein the rotatable blade housing is rotatable relative to the first and second electrodes.

10. The electrosurgical instrument according to claim 1, wherein the second electrode is formed of a plurality of electrodes.

11. An electrosurgical system, comprising:
    a source of electrosurgical energy; and
    an electrosurgical instrument configured to couple to the source of electrosurgical energy, the electrosurgical instrument comprising:
       a housing defining a longitudinal axis; and
       an electrode body coupled to the housing, the electrode body including:
          an electrode face formed on a distal-most end of the electrode body, wherein the entire electrode face defines a plane that is perpendicular to the longitudinal axis;
          a rotatable blade housing defining an opening;
          a blade longitudinally moveable with respect to the rotatable blade housing while the electrode body is treating tissue and configured to extend through the opening to dispose at least a portion of the blade distally beyond the electrode face;
          a first electrode disposed concentrically about the opening; and
          a second electrode disposed concentrically about the first electrode, the blade configured to rotate relative to the first and second electrodes.

12. The electrosurgical system according to claim 11, wherein the first and second electrodes are configured to connect to opposite electrical potentials of the source of electrosurgical energy.

13. The electrosurgical system according to claim 11, wherein the blade includes a bidirectional cutting surface.

14. The electrosurgical system according to claim 11, wherein the blade is configured to rotate relative to the electrode body while the electrode body is treating tissue.

15. The electrosurgical system according to claim 11, wherein the electrode body is cylindrically shaped.

16. The electrosurgical system according to claim 11, wherein the blade is configured to move longitudinally with respect to the rotatable blade housing between an undeployed position, wherein a distal end of the blade is disposed proximal to the electrode face, and a plurality of deployed positions, wherein at least a portion of the blade is disposed distally beyond the electrode face.

17. The electrosurgical system according to claim 16, wherein the electrosurgical instrument further comprises an actuator operably coupled to the blade and configured to move the blade between the undeployed position and the plurality of deployed positions.

18. The electrosurgical system according to claim 11, wherein the electrosurgical instrument further comprises at least one actuator configured to move the electrode body in at least one of a yaw direction, a pitch direction, and a rotation direction relative to the longitudinal axis.

19. The electrosurgical system according to claim 11, wherein the rotatable blade housing is rotatable relative to the first and second electrodes, the blade disposed within the rotatable blade housing.

20. The electrosurgical system according to claim 11, wherein the second electrode is formed of a plurality of electrodes.

\* \* \* \* \*